US012797381B2

(12) United States Patent
Toombs

(10) Patent No.: US 12,797,381 B2
(45) Date of Patent: Nov. 17, 2026

(54) METHODS OF TREATING OR PREVENTING CONDITIONS ASSOCIATED WITH OPIATE WITHDRAWAL OR OPIATE RELAPSE

(71) Applicant: Proniras Corporation, Seattle, WA (US)

(72) Inventor: Christopher Francis Toombs, Sammamish, WA (US)

(73) Assignee: Proniras Corporation, Seattle, WA (US)

( * ) Notice: Subject to any disclaimer, the term of this patent is extended or adjusted under 35 U.S.C. 154(b) by 250 days.

(21) Appl. No.: 18/566,736

(22) PCT Filed: Jun. 9, 2022

(86) PCT No.: PCT/US2022/032778

§ 371 (c)(1),
(2) Date: Dec. 4, 2023

(87) PCT Pub. No.: WO2022/261282

PCT Pub. Date: Dec. 15, 2022

(65) Prior Publication Data

US 2024/0277697 A1 Aug. 22, 2024

Related U.S. Application Data

(60) Provisional application No. 63/208,886, filed on Jun. 9, 2021.

(51) Int. Cl.
*A61K 31/4725* (2006.01)
*A61K 31/5513* (2006.01)
*A61P 25/36* (2006.01)

(52) U.S. Cl.
CPC ...... *A61K 31/4725* (2013.01); *A61K 31/5513* (2013.01); *A61P 25/36* (2018.01)

(58) Field of Classification Search
CPC .................................................. A61K 31/4725
See application file for complete search history.

(56) References Cited

U.S. PATENT DOCUMENTS

| | | | |
|---|---|---|---|
| 11,744,829 | B2 | 9/2023 | Braga et al. |
| 2002/0098179 | A1 | 7/2002 | Brearley et al. |
| 2005/0256155 | A1 | 11/2005 | Ornstein |
| 2017/0128446 | A1 | 5/2017 | Hansen et al. |
| 2019/0321351 | A1 | 10/2019 | Braga et al. |
| 2020/0030304 | A1 | 1/2020 | Rogawski et al. |
| 2024/0277696 | A1 | 8/2024 | Toombs |

FOREIGN PATENT DOCUMENTS

| | | | |
|---|---|---|---|
| JP | 2009509975 | A | 3/2009 |
| JP | 2017519827 | A | 7/2017 |
| JP | 2022135978 | A | 9/2022 |
| RU | 2202370 | C1 | 4/2003 |
| WO | WO-03091243 | A1 | 11/2003 |
| WO | WO-2007038551 | A2 | 4/2007 |
| WO | WO-2015197079 | A1 | 12/2015 |
| WO | WO-2017218344 | A1 | 12/2017 |
| WO | WO-2021087456 | A1 | 5/2021 |
| WO | WO-2022261282 | A1 | 12/2022 |
| WO | WO-2022261287 | A1 | 12/2022 |

OTHER PUBLICATIONS

Acri, et al., "Effects of ATDP 34,023 on Prime-Induced Reinstatement of Lever Pressing Previously Reinforced by Oxycodone in Rats," National Institute on Drug Abuse, Oct. 7, 2021, 10 pages.
Anis, et al., "The dissociative anaesthetics, ketamine and phencyclidine, selectively reduce excitation of central mammalian neurones by N-methyl-aspartate," Br J Pharmacol. Jun. 1983; 79(2):565-75.
Apland, et al., "Efficacy of the GluK1/AMPA Receptor Antagonist LY293558 against Seizures and Neuropathology in a Soman-Exposure Model without Pretreatment and its Pharmacokinetics after Intramuscular Administration," J Pharmacol Exp Ther, Jan. 2013; 344:133-140.
Apland, et al., "Soman Induces Icotgenesis In The Amygdala And Interictal Activity In The Hippocampus That Are Blocked By A GluR5 Kainate Receptor Antagonist In Vitro," Neuroscience 2009; 159:380-389.
Apland, et al., "The limitations of diazepam as a treatment for nerve agent-induced seizures and neuropathology in rats: comparison with UBP302," J Pharmacol Exp Ther. Nov. 2014; 351(2):359-72. Epub Aug. 25, 2014.
Aroniadou-Anderjaska, et al., "Long-term neuropathological and behavioral impairments after exposure to nerve agents," Ann NY Acad Sci. Jun. 2016; 1374(1):17-28. Epub Mar. 22, 2016.
ATNAA Package Insert/Prescribing Information, revised May 2020, 8 pages retrieved on Jul. 17, 2025 at: https://www.accessdata.fda.gov/drugsatfda_docs/label/2020/021175s041lbl.pdf.
Bettler, et al., "Cloning of a putative glutamate receptor: a low affinity kainate-binding subunit," Neuron. Feb. 1992; 8(2):257-65.
Bleakman, et al., "Kainate receptor pharmacology and physiology," Cell Mol Life Sci. Nov. 15, 1999; 56(7-8):558-66.
Bleakman, et al., "Neuropharmacology of AMPA and kainate receptors," Neuropharmacology. Oct.-Nov. 1998; 37(10-11):1187-204.
Brann, et al., "Excitatory amino acids: function and significance in reproduction and neuroendocrine regulation," Front Neuroendocrinol. Mar. 1994; 15(1):3-49.
CANA "Convulsant Antidote for Nerve Agent" Valium brand of dizepam tablets, Prescribing Information, 15 pages retrieved on Jul. 17, 2025 at: https://www.accessdata.fda.gov/drugsatfda_docs/label/2016/013263s094lbl.pdf.
Carlezon, et al., "AMPA antagonist LY293558 blocks the development, without blocking the expression, of behavioral sensitization to morphine," Synapse. Mar. 15, 1999; 31(4):256-62.

(Continued)

*Primary Examiner* — Golam M Shameem
(74) *Attorney, Agent, or Firm* — COOLEY LLP

(57) ABSTRACT

The present disclosure relates to methods of treating or preventing a condition (e.g., a symptom associated with opiate withdrawal or opiate relapse) in a subject, comprising administering to the subject a therapeutically effective amount of tezampanel, a pharmaceutically acceptable salt thereof, or a prodrug thereof.

27 Claims, 14 Drawing Sheets

(56) References Cited

OTHER PUBLICATIONS

Chapman, et al., "The anticonvulsant effect of the non-NMDA antagonists, NBQX and GYKI 52466, in mice," Epilepsy Res. Jul. 1991; 9(2):92-6.
Collingridge, et al., "Excitatory amino acid receptors in the vertebrate central nervous system," Pharmacol Rev. Jun. 1989; 41(2):143-210.
Dall, et al., "Interaction of the competitive AMPA receptor antagonist NBQX with hexobarbital," Pharmacol Biochem Behav. Sep. 1993; 46(1):73-6.
Duodote Prescribing Information, revised Nov. 2021, 12 pages retrieved on Jul. 17, 2025 at: https://www.accessdata.fda.gov/drugsatfda_docs/label/2022/021983Orig1s038lbl.pdf.
Egebjerg, et al., "Cloning of a cDNA for a glutamate receptor subunit activated by kainate but not AMPA," Nature. Jun. 27, 1991; 351(6329):745-8.
Figueiredo, et al., "The GluK1 (GluR5) Kainate/α-amino-3-hydroxy-5-methyl-4-isoxazolepropionic acid receptor antagonist LY293558 reduces soman-induced seizures and neuropathology," J Pharmacol Exp Ther. Feb. 2011; 336(2):303-12. Epub Oct. 20, 2010.
Fletcher, et al., "New developments in the molecular pharmacology of alpha-amino-3-hydroxy-5-methyl-4-isoxazole propionate and kainate receptors," Pharmacol Ther. 1996; 70(1):65-89.
Fountain, N.B., "Status epilepticus: risk factors and complications," Epilepsia. 2000; 41 Suppl 2:S23-S30.
Goodkin, et al., "Status epilepticus increases the intracellular accumulation of GABAA receptors," J Neurosci. Jun. 8, 2005; 25(23):5511-20.
Harrison, et al., "Quantitative studies on some antagonists of N-methyl D-aspartate in slices of rat cerebral cortex," Br J Pharmacol. Feb. 1985; 84(2):381-91.
Hollmann, et al., "Cloned glutamate receptors," Annu Rev Neurosci. 1994; 17:31-108.
Kest, et al., "The competitive alpha-amino-3-hydroxy-5-methylisoxazole-4-propionate receptor antagonist LY293558 attenuates and reverses analgesic tolerance to morphine but not to delta or kappa opioids," J Pharmacol Exp Ther. Dec. 1997; 283(3):1249-55.
Knezevic, et al., "Basic/Translational Development of Forthcoming Opioid- and Nonopioid-Targeted Pain Therapeutics," Anesth Analg. Nov. 2017; 125(5):1714-1732.
Lallement, et al., "Effects of soman-induced seizures on different extracellular amino acid levels and on glutamate uptake in rat hippocampus," Brain Res. Nov. 1, 1991; 563(1-2):234-40.
Lewis, et al., "Cardiovascular effects of the N-methyl-D-aspartate receptor antagonist MK-801 in conscious rats," Hypertension. Jun. 1989; 13(6 Pt 2):759-65.
McDonough, et al., "Neuropharmacological mechanisms of nerve agent-induced seizure and neuropathology," Neurosci Biobehav Rev. Sep. 1997; 21(5):559-79.
McDonough, et al., "Time-dependent reduction in the anticonvulsant effectiveness of diazepam against soman-induced seizures in guinea pigs," Drug Chem Toxicol. Jul. 2010; 33(3):279-83.
McFarlane, et al., "AMPA receptor competitive antagonism reduces halothane MAC in rats," Anesthesiology. Dec. 1992; 77(6):1165-70.
Mioduszewski, et al., Interaction of exposure concentration and duration in determining acute toxic effects of sarin vapor in rats. Toxicol Sci. Apr. 2002; 66(2):176-84.
O'Donnell, et al., "In vivo microdialysis and electroencephalographic activity in freely moving guinea pigs exposed to organophosphorus nerve agents sarin and VX: analysis of acetylcholine and glutamate," Arch Toxicol. Dec. 2011; 85(12):1607-16. Epub Jun. 22, 2011.
Ohtani, et al., "Post-traumatic stress disorder symptoms in victims of Tokyo subway attack: a 5-year follow-up study," Psychiatry Clin Neurosci. Dec. 2004; 58(6):624-9.
Olney, et al., "Pathological changes induced in cerebrocortical neurons by phencyclidine and related drugs," Science. Jun. 16, 1989; 244(4910):1360-2.
Protopam Chloride Prescribing Information, dated Sep. 8, 2010, 16 pages retrieved on Jul. 16, 2025 at: https://www.accessdata.fda.gov/drugsatfda_docs/label/2010/014134s022lbl.pdf.
Pyridostigmine Bromide Package Insert, revised Oct. 2024, 19 pages retrieved on Jul. 16, 2025 at: https://www.accessdata.fda.gov/drugsatfda_docs/label/2024/217604s000lbl.pdf.
Rasmussen, et al., "A Selective AMPA Antagonist, LY293558, Suppresses Morphine Withdrawal-Induced Activation of Locus Coeruleus Neurons and Behavioral Signs of Morphine Withdrawal," Neuropsychopharmacology 1996, vol. 15, No. 5, 9 pages.
Rogawski, et al., "Role of AMPA and GluR5 kainate receptors in the development and expression of amygdala kindling in the mouse," Neuropharmacology. 2001; 40(1):28-35.
Sang, et al., "LY293558, a novel AMPA/GluR5 antagonist, is efficacious and well-tolerated in acute migraine," Cephalalgia. Jul. 2004; 24(7):596-602.
Schiffer, et al., "Rat GluR7 and a carboxy-terminal splice variant, GluR7b, are functional kainate receptor subunits with a low sensitivity to glutamate, " Neuron. Nov. 1997; 19(5):1141-6.
Shih, et al., "Anticonvulsants for soman-induced seizure activity," J Biomed Sci. Mar.-Apr. 1999; 6(2):86-96.
Silbergleit, et al., "NETT Investigators. Intramuscular versus intravenous therapy for prehospital status epilepticus," N Engl J Med. Feb. 16, 2012; 366(7):591-600.
Snider, et al., "Assessing the therapeutic efficacy of oxime therapies against percutaneous organophosphorus pesticide and nerve agent challenges in the Hartley guinea pig," J Toxicol Sci. Dec. 2015; 40(6):759-75.
Sommer, et al., "A glutamate receptor channel with high affinity for domoate and kainate," EMBO J. Apr. 1992; 11(4):1651-6.
Vezzani, et al., "[3H]norepinephrine release from hippocampal slices is an in vitro biochemical tool for investigating the pharmacological properties of excitatory amino acid receptors," J Neurochem. Nov. 1987; 49(5):1438-42.
Wade, et al., "Changes in extracellular amino acids during soman- and kainic acid-induced seizures," J Neurochem. Aug. 1987; 49(2):645-50.
Weber, et al., "Evaluation of ketamine to reduce semi-acute electrophysiology and behavioral compromise following nerve agent exposure," Abstract No. 1625, The Toxicologist Supplement to Toxicological Sciences, 56th Annual Meeting and ToxExpo, Baltimore, Maryland, Mar. 12-16, 2017, 2 pages.
White, et al., "Evaluation of ATDP 34,023 to Attenuate Oxycodone-Precipitated Withdrawal Effects in Mice," National Institute on Drug Abuse, May 8, 2019, 8 pages.
Yamasue, et al., "Human brain structural change related to acute single exposure to sarin," Ann Neurol. Jan. 2007; 61(1):37-46.
Yanagisawa, et al., "Sarin experiences in Japan: acute toxicity and long-term effects," J Neurol Sci. Nov. 1, 2006; 249(1):76-85. Epub Sep. 7, 2006.
Author Unknown, "HHS partners to develop new treatment for seizures caused by nerve agents," Apr. 27, 2018, U.S. Department of Health & Human Services, Office of the Assistant Secretary for Preparedness and Response, [Retrieved from Internet on Mar. 31, 2026 at URL: https://us.pagefreezer.com/en-US/wa/browse/0a7f82bb-be6e-448a-ae11-373d22c37842find-by-timestamp=2020-12-31T08:51:59Z&url=https:%2F%2Fwww.hhs.gov%2Fabout%2Fnews%2F2018%2F04%2F27%2Fhhs-partners-develop-new-treatment-seizures-caused-nerve-agents.html&timestamp=2020-12-31T03:43:02Z], 2 pages.
Belikov, "Pharmaceutical Chemistry," Moscow High School, 1993, vol. 1, pp. 43-47, 14 pages total with English translation.
Bloomberg, et al., "HHS to Develop New Treatment for Seizures Caused by Nerve Agents," Apr. 27, 2018, 2 pages retrieved on Aug. 12, 2022 from the Internet at: https://www.bloomberg.com/press-releases/2018-04-27/hhs-to-develop-new-treatment-for%ADseizures-caused-by-nerve-agents.
Clinical Trials Arena, "Migraine drug could prove effective against nerve agents," Apr. 30, 2018, [Retrieved from Internet on Mar. 31, 2026 at URL: https://www.clinicaltrialsarena.com/news/migraine-drug-prove-effective-nerve-agents/?cf-view], 5 pages.
EP Application No. 22821005.0, Extended European Search Report mailed Mar. 17, 2025, Applicant Proniras Corporation; 8 pages.

(56) References Cited

OTHER PUBLICATIONS

EP Application No. 22821009.2, Extended European Search Report mailed Mar. 18, 2025, Applicant Proniras Corporation; 9 pages.
Ivanets, "A Comprehensive Approach in the Treatment of Opiate Withdrawal Syndrome," Vrach, 2008(7), National Research Center on Addictions, Ministry of Health of the Russian Federation, 11 pages with English translation.
JP Application No. 2023-575914, Search Report mailed May 21, 2026, Applicant: Proniras Corporation, 25 pages with English translation.
Kharkevich, Pharmacology: Textbook, 2010, 10th ed., Moscow: GEOTAR-Media, pp. 72-82, 32 pages total with English translation.
Opioid Oral Morphine Milligram Equivalent (MME) Conversion Factors, 2 pages retrieved on May 28, 2026 from the Internet at URL: https://medicaid-documents.dhhs.utah.gov/Documents/files/Opioid-Morphine-EQ-Conversion-Factors.pdf.
PCT Application No. PCT/US2022/032778, International Preliminary Report on Patentability mailed Nov. 21, 2023, Applicant Proniras Corporation; 5 pages.
PCT Application No. PCT/US2022/32778, International Search Report and Written Opinion mailed Aug. 30, 2022, Applicant Proniras Corporation; 8 pages.
PCT Application No. PCT/US2022/32783, International Preliminary Report on Patentability mailed Dec. 21, 2023, Applicant Proniras Corporation; 8 pages.
PCT Application No. PCT/US2022/32783, International Search Report and Written Opinion mailed Sep. 13, 2022, Applicant Proniras Corporation; 10 pages.
Prokofieva, et al., "Course of Lectures on General Pharmacology: Educational and Methodological Manual," (UIGU, Ulyanovsk, 2017), 6 pages with English translation.
RU Application No. 2023135655, Search Report mailed Nov. 14, 2025, Applicant: Proniras Corporation, 6 pages with English translation.
RU Application No. 2023135766, Search Report mailed Dec. 17, 2025, Applicant: Proniras Corporation, 4 pages with English translation.
Schmidt, D., "Effect of antiepileptic drugs on the postictal state. A critical overview," Epilepsy Behav. Oct. 2010; 19(2):176-81. Epub Aug. 7, 2010.
Trescot, et al., "Opioid pharmacology," Pain Physician. Mar. 2008; 11(2 Suppl):S133-53.
U.S. Appl. No. 19/320,986, filed Sep. 5, 2025; Inventor Braga, et al.
Vandergriff, et al., "The Selective mGlu2/3 Receptor Agonist LY354740 Attenuates Morphine-withdrawal-induced Activation of Locus Coeruleus Neurons and Behavioral Signs of Morphine Withdrawal," Neuropharmacology. Feb. 1999; 38(2):217-22.
WHO Guidelines for the Pharmacological and Radiotherapeutic Management of Cancer Pain in Adults and Adolescents. Geneva: World Health Organization; 2018. Table A6.2, Approximate potency of opioids relative to morphine; PO and immediate-release formulations unless stated otherwisea. 144 pages retrieved from the Internet on May 28, 2026 at URL: https://www.ncbi.nlm.nih.gov/books/NBK537482/table/appannex6.tab2/.

METHODS OF TREATING OR PREVENTING CONDITIONS ASSOCIATED WITH OPIATE WITHDRAWAL OR OPIATE RELAPSE

RELATED APPLICATION

This application is a U.S. National Stage Application under 35 U.S.C. § 371 of International Application No. PCT/US2022/032778, filed Jun. 9, 2022, which claims the benefit of priority to U.S. Provisional Application No. 63/208,886, filed Jun. 9, 2021, the disclosures of which are incorporated herein by reference.

GOVERNMENT SUPPORT

This invention was made with government support under UG3DA050923 awarded by National Institute on Drug Abuse. The government has certain rights in the invention.

BACKGROUND

Opioids are drugs such as morphine, codeine, oxycodone, and methadone. While these drugs are highly effective in relief of acute pain and chronic pain management, physical dependence can develop in as briefly as one week of continued use. Upon abrupt cessation of opiate administration following a period of sub-acute or chronic use, an established physical dependence can lead to a withdrawal state. Symptoms of opiate withdrawal can emerge within 24 hours and can include many perturbations of normal sense of self and wellness that may very quickly deteriorate into a constellation of adversely perceived physiologic alterations or sensations, such as runny nose, watery eyes and yawning, restlessness or anxiety, irritability or mood disturbances, increased pain, goose bumps on the skin, chills or sweating, stomach cramps, nausea, vomiting or diarrhea, muscle cramping or aches and joint pain, tremors or muscle twitching, tachycardia, hypertension, insomnia, and suicidal ideation. The severity of opiate withdrawal symptoms can range from mild to moderate and severe, and is often dependent on the duration of opiate use and/or abuse and the opiate that was being administered. While opiate withdrawal can be excruciatingly difficult for the individual suffering, the symptoms are not usually life-threatening. However, the symptoms of opiate withdrawal can amount to a severity that individuals who have become habituated to opioids are propelled into a continuation of opioid use and/or abuse and, sadly, prefer to remain in a state of addiction rather than attempt to endure the anticipated and well-known torturous physical symptoms of opiate withdrawal. And in cases where an individual braves the conditions of opiate withdrawal and attempts to begin a sober life, it is common that other factors (inappropriate social circles) will lead an individual to relapse into opiate use/abuse once again.

There is thus a need for treatment or prevention of both opiate withdrawal and relapse. The

SUMMARY

In some aspects, the present disclosure provides a method of treating or preventing a condition (e.g., a symptom associated with opiate withdrawal or opiate relapse) in a subject, comprising administering to the subject a therapeutically effective amount of tezampanel, a pharmaceutically acceptable salt thereof, or a prodrug thereof.

In some aspects, the present disclosure provides tezampanel, a pharmaceutically acceptable salt thereof, or a prodrug thereof for use in the treatment or prevention of a condition (e.g., a symptom associated with opiate withdrawal or opiate relapse) in a subject.

In some aspects, the present disclosure provides use of tezampanel, a pharmaceutically acceptable salt thereof, or a prodrug thereof, in the manufacture of a medicament for the treatment or prevention of a condition (e.g., a symptom associated with opiate withdrawal or opiate relapse) in a subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

Denotes significantly different from the group chronically administered saline b.i.d.+vehicle, =p≤0.01; * Denotes significantly different from the group chronically administered saline b.i.d.+vehicle, *=p≤0.05. Veh=Vehicle; BWT=Body weight.

Figure 4A:
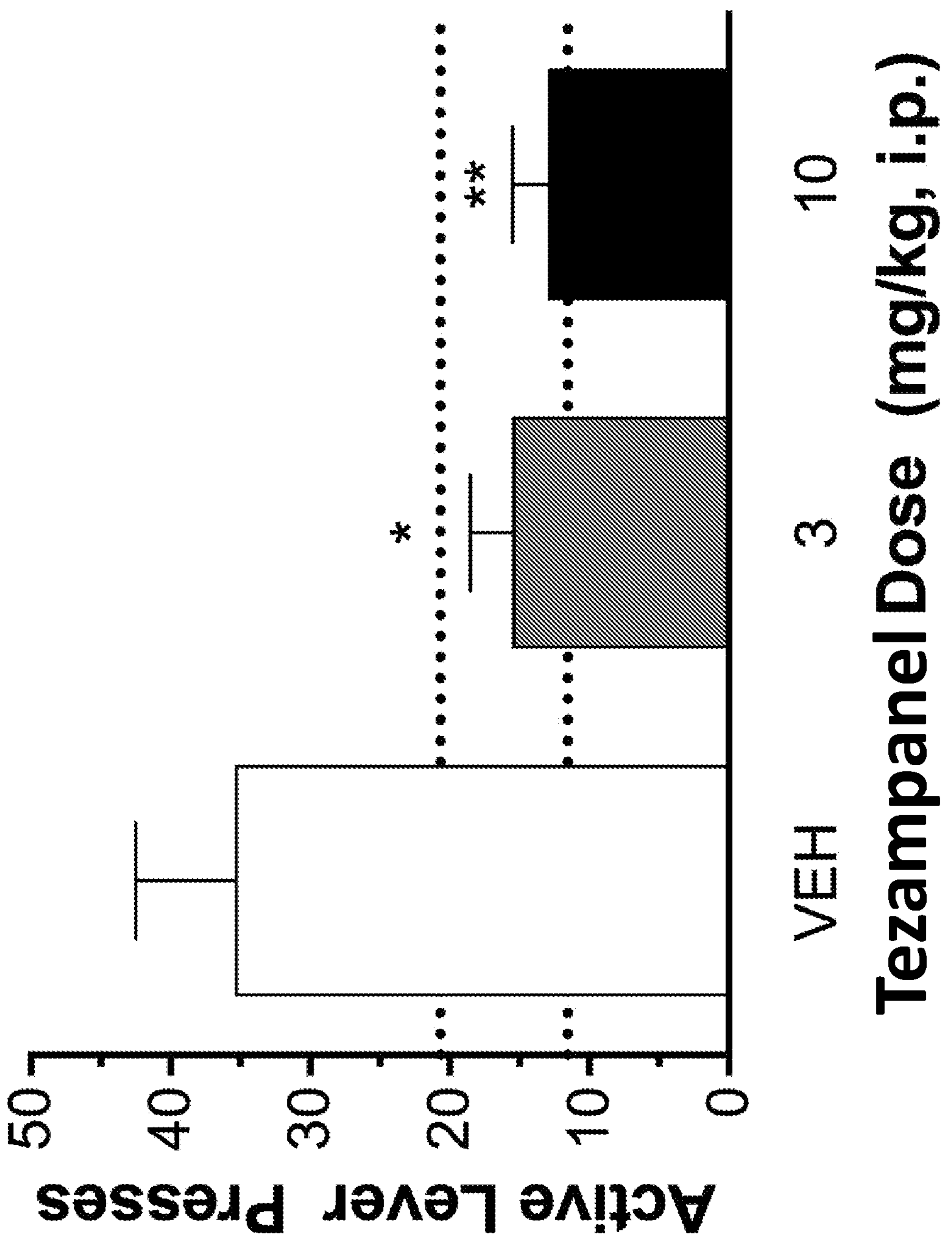

FIG. 4A is a graph showing the mean number of active lever presses during the oxycodone prime-induced reinstatement test session as a function of tezampanel dose. Brackets through the bars indicate ±SEM. "VEH"=results of the vehicle-treatment group. Dashed horizontal lines indicate the range of the means of active lever presses across dosage groups occurring during the last session of extinction. Asterisks indicate *P≤0.05 and **P≤0.01 relative to VEH.

Figure 4B:
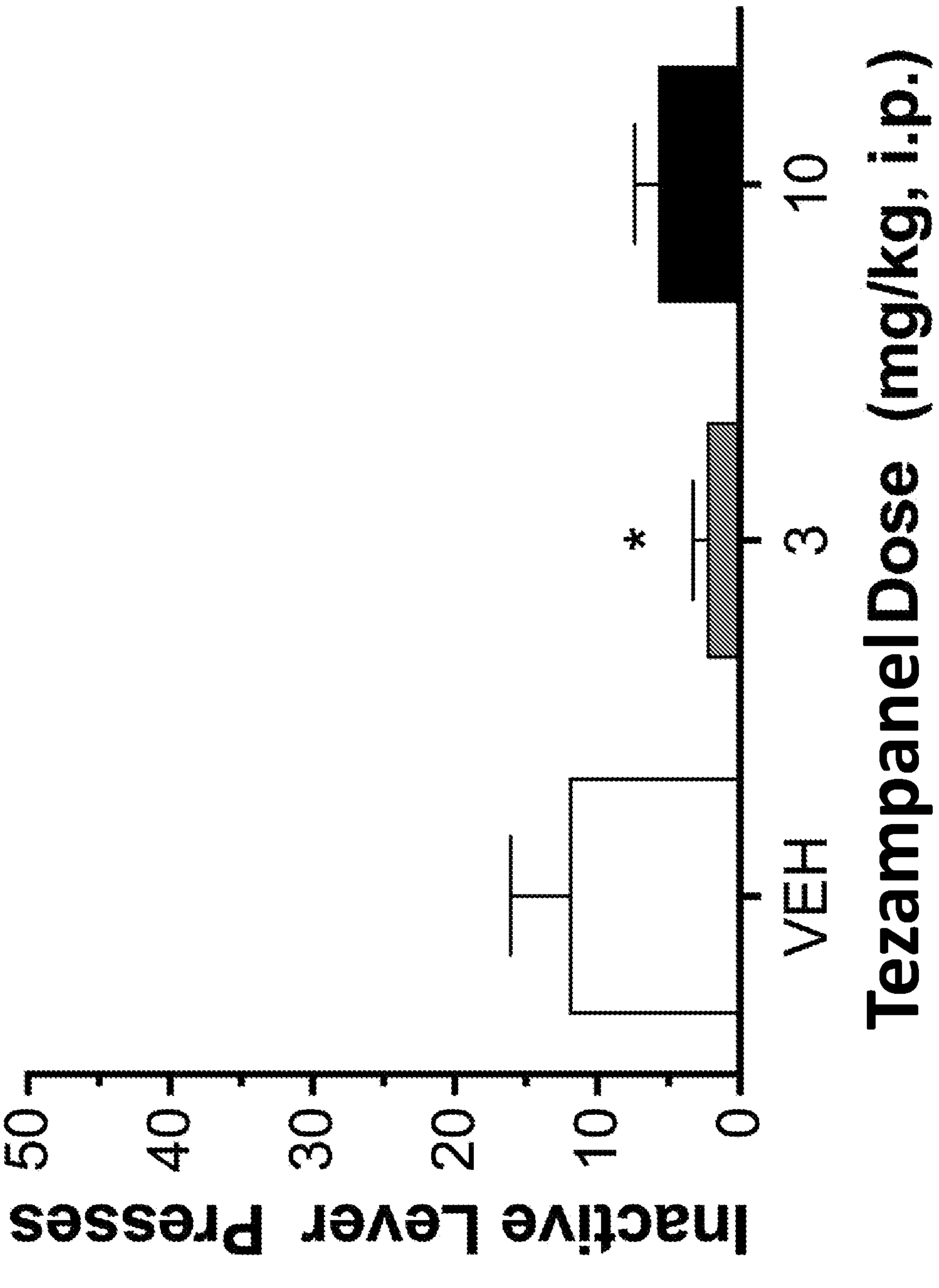

FIG. 4B is a graph showing the mean number of inactive lever presses during the oxycodone prime-induced reinstatement test session as a function of tezampanel dose.

DETAILED DESCRIPTION

Opioids are drugs that are exceptionally effective in suppressing activity in the central nervous system (CNS) and withdrawal from sub-acute or chronic use of such agents can elicit symptoms of withdrawal which are largely driven by a rebound excitatory state that develops within the CNS upon abrupt cessation of their use. Glutamate is an amino acid that serves as the predominant excitatory neurotransmitter in the CNS, in part exerting its effects at one of three types of ionotropic glutamate receptors which are ligand-gated ion channels called NMDA receptors, AMPA receptors, and kainate receptors.

Tezampanel is a competitive antagonist of glutamate signalling predominantly at AMPA and kainate receptors, but also with some antagonist activity at NMDA receptors. By antagonizing the CNS effects of the major excitatory neurotransmitter glutamate, tezampanel may blunt the glutamate-driven symptoms of opiate withdrawal. The administration of tezampanel achieves this uniquely by pharmacologically blunting an underlying and overt hyperexcitation of the CNS during withdrawal which is driven by overt and excessive glutamate signalling in the CNS.

In some aspects, the present disclosure provides a method of treating or preventing a condition (e.g., a symptom associated with opiate withdrawal or opiate relapse) in a subject, comprising administering to the subject a therapeutically effective amount of tezampanel, a pharmaceutically acceptable salt thereof, or a prodrug thereof.

In some aspects, the present disclosure provides tezampanel, a pharmaceutically acceptable salt thereof, or a prodrug thereof for use in the treatment or prevention of a condition (e.g., a symptom associated with opiate withdrawal or opiate relapse) in a subject.

In some aspects, the present disclosure provides use of tezampanel, a pharmaceutically acceptable salt thereof, or a prodrug thereof, in the manufacture of a medicament for the treatment or prevention of a condition (e.g., a symptom associated with opiate withdrawal or opiate relapse) in a subject.

Treated Subjects and Conditions

In some embodiments, the subject is an animal.

In some embodiments, the subject is a human.

In some embodiments, the subject is an adult.

In some embodiments, the subject has an age ranging from 18 years to 65 years.

In some embodiments, the subject has a history of opiate use or abuse.

In some embodiments, the subject is a child.

In some embodiments, the subject has an age younger than 18 years.

In some embodiments, the subject is an infant.

In some embodiments, the subject has an age of 2 years or younger.

In some embodiments, the subject has an age of 1 year or younger.

In some embodiments, the subject has an age of 9 months or younger, 6 months or younger, 5 months or younger, 4 months or younger, 3 months or younger, 2 months or younger, or 1 month or younger.

In some embodiments, the maternal parent of the subject (e.g., the infant) has a history of opiate use or abuse.

In some embodiments, the subject (e.g., the infant) has been subjected to in-utero exposure to the opiate.

In some embodiments, the condition is associated with opiate withdrawal.

In some embodiments, the condition is a symptom associated with opiate withdrawal.

In some embodiments, the subject has a previous recovery from opiate use or abuse.

In some embodiments, the condition is associated with opiate relapse.

In some embodiments, the condition is a symptom associated with opiate relapse.

In some embodiments, the condition is associated with a disease.

In some embodiments, the condition is a symptom of a disease.

Opiate Withdrawal and Opiate Relapse

The term "opiate withdrawal", as used herein, refers to one or more symptoms arising from the sudden cessation or reduction of opioid usage. The term "opiate relapse", as used herein, refers to one or more symptoms arising from a deterioration of opioid usage after a period of improvement (e.g., previously reduced or abstinence from opioid usage).

In some embodiments, the subject does not intake the opiate within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

In some embodiments, the subject has a reduced urine concentration for the opiate, as measured by urinalysis (e.g., point of care (POC) urinalysis), within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

In some embodiments, the subject is substantially free of the opiate, as measured by urinalysis (e.g., point of care (POC) urinalysis), within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

In some embodiments, the subject has a urine concentration for the opiate being lower than about 2000 ng/ml, about 1500 ng/ml, about 1000 ng/ml, about 500 ng/ml, about 400 ng/ml, about 300 ng/ml, about 200 ng/ml, about 100 ng/ml, about 50 ng/ml, about 25 ng/ml, or about 10 ng/ml, as measured by urinalysis (e.g., point of care (POC) urinalysis) within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

In some embodiments, the subject has a urine concentration for the opiate being lower than the cutoff levels described in Table 1, as measured by urinalysis (e.g., point of care (POC) urinalysis) within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

In some embodiments, the subject does not intake the opiate during the treatment or prevention.

In some embodiments, the subject intakes the opiate during the treatment or prevention.

In some embodiments, the subject has an increased urine concentration for the opiate, as measured by urinalysis (e.g., point of care (POC) urinalysis), during the treatment or prevention.

In some embodiments, the subject has a urine concentration for the opiate being lower than about 2000 ng/ml, about 1500 ng/ml, about 1000 ng/ml, about 500 ng/ml, about 400 ng/ml, about 300 ng/ml, about 200 ng/ml, about 100 ng/ml, about 50 ng/ml, about 25 ng/ml, or about 10 ng/ml, as measured by urinalysis (e.g., point of care (POC) urinalysis) during the treatment or prevention.

In some embodiments, the subject has a urine concentration for the opiate being lower than the urinalysis detection limits (cutoff levels), examples of which are described in Table 1, as measured by urinalysis (e.g., point of care (POC) urinalysis) during the treatment or prevention.

TABLE 1

| Opiate | Cutoff Level (POC Urinalysis) |
|---|---|
| Methadone | 50 ng/ml |
| Morphine | 300 ng/ml |
| Oxycodone | 100 ng/ml |
| Opiates (Generic) | 2000 ng/ml |

In some embodiments, the opiate is codeine, heroin, hydrocodone (e.g., Vicodin), hydromorphone (e.g., Dilaudid), methadone, meperidine (e.g., Demerol), morphine, or oxycodone (e.g., Percocet or Oxycontin).

In some embodiments, the opiate withdrawal is codeine withdrawal, heroin withdrawal, hydrocodone (e.g., Vicodin) withdrawal, hydromorphone (e.g., Dilaudid) withdrawal, methadone withdrawal, meperidine (e.g., Demerol) withdrawal, morphine withdrawal, or oxycodone (e.g., Percocet or Oxycontin) withdrawal.

In some embodiments, the opiate withdrawal is codeine relapse, heroin relapse, hydrocodone (e.g., Vicodin) relapse, hydromorphone (e.g., Dilaudid) relapse, methadone relapse, meperidine (e.g., Demerol) relapse, morphine relapse, or oxycodone (e.g., Percocet or Oxycontin) relapse.

In some embodiments, the symptom is drug craving, anxiety, nausea, vomiting, pain (e.g., muscle ache), diarrhea, sweating, sneezing, fever, or an increased heart rate.

In some embodiments, the administration reduces the frequency, severity, and/or duration of the symptom associated with opiate withdrawal.

In some embodiments, the frequency, severity, and/or duration of the symptom associated with opiate withdrawal is measured by Clinical Opiate Withdrawal Scale (COWS).

It is understood that Clinical Opiate Withdrawal Scale (COWS) refers to a method known to the skilled artisan in the technic field (e.g., a registered practitioner) to measure the frequency, severity, and/or duration of a patient's opiate withdrawal symptom (Wesson, D. R., & Ling, W. (2003). The Clinical Opiate Withdrawal Scale (COWS). J. Psychoactive Drugs, 35(2), 253-9). COWS uses an 11-item scale to rate common signs and symptoms of opiate withdrawal. The summed score for the complete scale can be used to assess the severity of withdrawal and assess the level of physical dependence on opioids. The maximum COWS score is 48.

In some embodiments, the COWS score is measured as described in Table 2 below:

TABLE 2

| Category | Exemplary Examination |
|---|---|
| Resting Pulse Rate | This is the first symptom that is tested once the patient has been sitting down or lying down for at least a minute. The normal range would be between 80-bpm if not less than that (depending on their age and weight) in which case would be scored 0. A pulse that exceeds the 120-bpm mark is given a score of 4. |
| Gastrointestinal Upset | This is also a fundamental part of the assessment as this is the body's way to tell you something is wrong and is rated based on the last half an hour. If they feel no symptoms of nausea or gastrointestinal irritation, they get a score of 0. Moreover, if they experience consistent episodes of nonstop vomiting or diarrhea, they will be given a score of 5 as this is one way of the body rejecting what was consumed. |
| Sweating | The rate of patient sweat is scored based on the last half an hour with disregard to any physical fitness activity or a rise in room temperature. Similarly, to the previous topic, 0 is scored if patient's body temperature is within the normal range of ~37° C. and if they are showing any signs of uncontrollable chills or sweat streaming down their face and body, a score of 4 is given. |
| Tremor | This refers to the unusual movements of the body. If patient is in stable condition with no odd movements then they are given a score of 0 but if they are experiencing tremor and muscle twitches throughout examination, they get a score of 4. |
| Restlessness | This part of the scale is examined throughout the duration of the assessment. If the patient can remain calm and sit still through the test, they will be given a score of 0. However, if they are quite agitated, restless and cannot sit still throughout the examination, they will be given a score of 5. |
| Yawning | This is an easy part of the assessment but requires focus to detail as this symptom should be monitored throughout the test. No yawning is an indication of a score of 0, whereas a score of 4 specifies the patient has constantly been yawning throughout the process of the test. |
| Pupil Size | This is a crucial feature to notice as the dilation size of the pupil can provide a sufficient amount of information. If the pupil is at a normal size, then they will be given a score of 0. If their pupils are dilated all the way and the iris is barely visible, a score of 5 will be given as this indicates that the ciliary muscle of the eye is temporarily paralysed and therefore the pupils cannot constrict as a result of misuse or overuse of addictive medications. |
| Anxiety or Irritability | This section is fairly similar to the restlessness section however the main difference to consider is if the patient cannot participate in the test because it is difficult for them to focus or sit still because they are irritated or anxious are score of 0 will be given. If the opposite occurs and they don't have any symptom, they get a score of 0. |
| Bone or Joint Aches | This section does not take into account any previous medical condition such as osteoporosis or osteoarthritis, it only examines any recent or new joint pains and aches that have occurred. If there are no signs of pain, 0 is |

TABLE 2-continued

| Category | Exemplary Examination |
| --- | --- |
| | given. If they are unable to sit in a still position due to pain discomfort or if they are holding on to area of pain a score of 4 will be given. |
| Gooseflesh Skin | This takes into account the texture of the skin. The condition and texture need to be examined as it can identify if they are cold, in shock or if they are frightened. If they have smooth skin, they are given 0. If they have very defined and visible piloerection skin due involuntary muscle contraction near the patient's hair follicles, they will be given a score of 5. |
| Runny Nose or Tearing | Much like the yawning section, this is also a fairly straightforward part to examine. Previous medical history of allergies or cold and flu symptoms are disregarded. If there are no signs or symptoms, 0 is given. If they are continuously sniffing or have an aggressive runny nose and runny eyes, 4 is given. |
| Total | All of the scores given will then be added up and a total score is given. Any total score in between 0-36 is categorised into 3 groups (5-12, 13-24 and 25-36) and based on which category the patient falls under, the severity of condition is diagnosed (mild, moderate and moderately severe). |

In some embodiments, prior to administration, the symptom associated with opiate withdrawal has a COWS score of about 5 or greater, about 6 or greater, about 7 or greater, about 8 or greater, about 9 or greater, about 10 or greater, about 11 or greater, or about 12 or greater.

In some embodiments, prior to administration, the symptom associated with opiate withdrawal has a COWS score of about 13 or greater, about 14 or greater, about 15 or greater, about 16 or greater, about 17 or greater, about 18 or greater, about 19 or greater, about 20 or greater, about 21 or greater, about 22 or greater, about 23 or greater, or about 24 or greater.

In some embodiments, prior to administration, the symptom associated with opiate withdrawal has a COWS score of about 25 or greater, about 26 or greater, about 27 or greater, about 28 or greater, about 29 or greater, about 30 or greater, about 31 or greater, about 32 or greater, about 33 or greater, about 34 or greater, or about 35 or greater.

In some embodiments, the administration reduces the frequency, severity, and/or duration of the symptom associated with opiate withdrawal, as measured by a COWS score, by about 1 or greater, about 2 or greater, about 3 or greater, about 4 or greater, about 5 or greater, about 6 or greater, about 7 or greater, about 8 or greater, about 9 or greater, about 10 or greater, about 11 or greater, about 12 or greater, about 13 or greater, about 14 or greater, about 15 or greater, about 16 or greater, about 17 or greater, about 18 or greater, about 19 or greater, about 20 or greater, about 21 or greater, about 22 or greater, about 23 or greater, about 24 or greater, about 25 or greater, about 26 or greater, about 27 or greater, about 28 or greater, about 29 or greater, about 30 or greater, about 31 or greater, about 32 or greater, about 33 or greater, about 34 or greater, or about 35 or greater.

In some embodiments, the administration reduces the frequency, severity, and/or duration of the symptom associated with opiate withdrawal, as measured by a COWS score, by about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36.

In some embodiments, the administration results into a reduced symptom associated with opiate withdrawal having a COWS score of about 35 or less, about 34 or less, about 33 or less, about 32 or less, about 31 or less, about 30 or less, about 29 or less, about 28 or less, about 27 or less, about 26 or less, or about 25 or less.

In some embodiments, the administration results into a reduced symptom associated with opiate withdrawal having a COWS score of about 24 or less, about 23 or less, about 22 or less, about 21 or less, about 20 or less, about 19 or less, about 18 or less, about 17 or less, about 16 or less, about 15 or less, about 14 or less, or about 13 or less.

In some embodiments, the administration results into a reduced symptom associated with opiate withdrawal having a COWS score of about 12 or less, about 11 or less, about 10 or less, about 9 or less, about 8 or less, about 7 or less, about 6 or less, about 5 or less, about 4 or less, about 3 or less, about 2 or less, or about 1 or less.

In some embodiments, the administration reduces the frequency, severity, and/or duration of the symptom associated with opiate relapse.

In some embodiments, the administration results in an avoidance or a reduction of adverse scoring (e.g., as can be documented on the Brief Substance Craving Scale (BSCS)).

In some embodiments, the administration results in an avoidance of adverse scoring (e.g., as can be documented on the Brief Substance Craving Scale (BSCS)).

In some embodiments, the administration results in a reduction of adverse scoring (e.g., as can be documented on the Brief Substance Craving Scale (BSCS)) by at least 1, at least 2, at least 3, at least 4, at least 5, at least 6, at least 7, at least 8, at least 9, at least 10, or at least 11.

In some embodiments, the administration results in an adverse scoring (e.g., as can be documented on the Brief Substance Craving Scale (BSCS)) of about 11 or less, about 10 or less, about 9 or less, about 8 or less, about 7 or less, about 6 or less, about 5 or less, about 4 or less, about 3 or less, about 2 or less, or about 1 or less.

Administration of Tezampanel

In some embodiments, the therapeutically effective amount of tezampanel, the pharmaceutically acceptable salt thereof, or the prodrug thereof alleviates an adversing drug-drug interation (DDI) between tezampanel and the opiate.

In some embodiments, the adversing drug-drug interation (DDI) is central nervous system (CNS) depression.

In some embodiments, the adversing drug-drug interation (DDI) is respiratory depression.

In some embodiments, the adversing drug-drug interation (DDI) is muscle weakness, lethargy, dizziness, disorientation, slurred speech or stuttering, reduced breathing rate, reduced heart rate, constipation, dry mouth, restlessness, agitation, euphoria, blurred vision, altered vision, double vision, memory loss, nausea, vomiting, or any combination thereof.

In some embodiments, tezampanel, the pharmaceutically acceptable salt thereof, or the prodrug thereof is administered in an oral dosage form (e.g., a tablet).

In some embodiments, the prodrug of tezampanel is dasolampenel or a pharmaceutically acceptable salt thereof.

In some embodiments, a therapeutically effective amount of dasolampanel, or the pharmaceutically acceptable salt thereof, is administered in an oral dosage form (e.g., a tablet).

In some embodiments, tezampanel, the pharmaceutically acceptable salt thereof, or the prodrug thereof is administered in a parenteral dosage form.

In some embodiments, tezampanel, the pharmaceutically acceptable salt thereof, or the prodrug thereof is administered in an intravenous (IV) dosage form, an intramuscular (IM) dosage form, a subcutaneous (SC) dosage form, or an intradermal (ID) dosage form.

In some embodiments, tezampanel, the pharmaceutically acceptable salt thereof, or the prodrug thereof is administered once during the treatment or prevention.

In some embodiments, tezampanel, the pharmaceutically acceptable salt thereof, or the prodrug thereof is administered two or more times during the treatment or prevention.

In some embodiments, tezampanel, the pharmaceutically acceptable salt thereof, or the prodrug thereof is administered every one hour, every two hours, every three hours, every four hours, every five hours, every six hours, every seven hours, every eight hours, every nine hours, every ten hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, or every 24 hours.

In some embodiments, tezampanel, the pharmaceutically acceptable salt thereof, or the prodrug thereof is administered at a dosage of about 0.10 mg/kg to about 10.0 mg/kg, about 0.15 mg/kg to about 7.5 mg/kg, about 0.20 mg/kg to about 5.0 mg/kg, about 0.25 mg/kg to about 2.5 mg/kg, about 0.30 mg/kg to about 2.0 mg/kg, about 0.35 mg/kg to about 1.85 mg/kg, about 0.40 mg/kg to about 1.70 mg/kg, about 0.45 mg/kg to about 1.65 mg/kg, about 0.50 mg/kg to about 1.60 mg/kg, about 0.55 mg/kg to about 1.55 mg/kg, about 0.65 mg/kg to about 1.50 mg/kg, about 0.70 mg/kg to about 1.45 mg/kg, about 0.75 mg/kg to about 1.40 mg/kg, about 0.80 mg/kg to about 1.35 mg/kg, about 0.85 mg/kg to about 1.30 mg/kg, about 0.90 mg/kg to about 1.25 mg/kg, about 0.95 mg/kg to about 1.20 mg/kg, about 1.00 mg/kg to about 1.15 mg/kg, or about 1.05 mg/kg to about 1.10 mg/kg.

In some embodiments, tezampanel, the pharmaceutically acceptable salt thereof, or the prodrug thereof is administered at a dosage of about 1.50 mg/kg to about 2.00 mg/kg, about 1.60 to about 1.95 mg/kg, about 1.70 mg/kg to about 1.90 mg/kg, or about 1.80 mg/kg to about 1.80 mg/kg.

In some embodiments, tezampanel, the pharmaceutically acceptable salt thereof, or the prodrug thereof is administered at a dosage of about 1.00 mg/kg to about 2.00 mg/kg, about 1.25 mg/kg to about 1.90 mg/kg, about 1.50 mg/kg to about 1.80 mg/kg, about 1.60 mg/kg to about 1.75 mg/kg, or about 1.65 mg/kg to about 1.70 mg/kg.

In some embodiments, tezampanel, the pharmaceutically acceptable salt thereof, or the prodrug thereof is administered at a dosage of about 0.05 mg/kg to about 0.50 mg/kg, about 0.10 mg/kg to about 0.40 mg/kg, about 0.15 mg/kg to about 0.30 mg/kg, or about 0.15 mg/kg to about 0.20 mg/kg.

In some embodiments, tezampanel, the pharmaceutically acceptable salt thereof, or the prodrug thereof is administered at a dosage of about 10.0 mg/kg or less, about 7.5 mg/kg or less, about 5.0 mg/kg or less, about 2.5 mg/kg or less, 2.00 mg/kg or less, about 1.95 mg/kg or less, about 1.90 mg/kg or less, about 1.85 mg/kg or less, about 1.80 mg/kg or less, about 1.75 mg/kg or less, about 1.70 mg/kg or less, about 1.65 mg/kg or less, about 1.60 mg/kg or less, about 1.55 mg/kg or less, about 1.50 mg/kg or less, about 1.45 mg/kg or less, about 1.40 mg/kg or less, about 1.35 mg/kg or less, about 1.30 mg/kg or less, about 1.25 mg/kg or less, about 1.20 mg/kg or less, about 1.15 mg/kg or less, about 1.10 mg/kg or less, about 1.05 mg/kg or less, about 1.00 mg/kg or less, about 0.95 mg/kg or less, about 0.90 mg/kg or less, about 0.85 mg/kg or less, about 0.80 mg/kg or less, about 0.75 mg/kg or less, about 0.70 mg/kg or less, about 0.65 mg/kg or less, about 0.60 mg/kg or less, about 0.55 mg/kg or less, about 0.50 mg/kg or less, about 0.45 mg/kg or less, about 0.40 mg/kg or less, about 0.35 mg/kg or less, about 0.30 mg/kg or less, about 0.25 mg/kg or less, about 0.20 mg/kg or less, about 0.15 mg/kg or less, or about 0.10 mg/kg or less.

In some embodiments, tezampanel, the pharmaceutically acceptable salt thereof, or the prodrug thereof is administered at a dosage of:

- about 10.0±1.0 mg/kg, about 10.0±0.9 mg/kg, about 10.0±0.8 mg/kg, about 10.0±0.7 mg/kg, about 10.0±0.6 mg/kg, about 10.0±0.5 mg/kg, about 10.0±0.4 mg/kg, about 10.0±0.3 mg/kg, about 10.0±0.2 mg/kg, or about 10.0±0.1 mg/kg (e.g., about 10.0 mg/kg);
- about 7.5±1.0 mg/kg, about 7.5±0.9 mg/kg, about 7.5±0.8 mg/kg, about 7.5±0.7 mg/kg, about 7.5±0.6 mg/kg, about 7.5±0.5 mg/kg, about 7.5±0.4 mg/kg, about 7.5±0.3 mg/kg, about 7.5±0.2 mg/kg, or about 7.5±0.1 mg/kg (e.g., about 7.5 mg/kg);
- about 5.0±2.0 mg/kg, about 5.0±1.5 mg/kg, about 5.0±1.0 mg/kg, about 5.0±0.9 mg/kg, about 5.0±0.8 mg/kg, about 5.0±0.7 mg/kg, about 5.0±0.6 mg/kg, about 5.0±0.5 mg/kg, about 5.0±0.4 mg/kg, about 5.0±0.3 mg/kg, about 5.0±0.2 mg/kg, or about 5.0±0.1 mg/kg (e.g., about 5.0 mg/kg);
- about 2.5±1.0 mg/kg, about 2.5±0.9 mg/kg, about 2.5±0.8 mg/kg, about 2.5±0.7 mg/kg, about 2.5±0.6 mg/kg, about 2.5±0.5 mg/kg, about 2.5±0.4 mg/kg, about 2.5±0.3 mg/kg, about 2.5±0.2 mg/kg, or about 2.5±0.1 mg/kg (e.g., about 2.5 mg/kg);
- about 1.83±1.0 mg/kg, about 1.83±0.9 mg/kg, about 1.83±0.8 mg/kg, about 1.83±0.7 mg/kg, about 1.83±0.6 mg/kg, about 1.83±0.5 mg/kg, about 1.83±0.4 mg/kg, about 1.83±0.3 mg/kg, about 1.83±0.2 mg/kg, or about 1.83±0.1 mg/kg (e.g., about 1.83 mg/kg);
- about 1.67±1.0 mg/kg, about 1.67±0.9 mg/kg, about 1.67±0.8 mg/kg, about 1.67±0.7 mg/kg, about 1.67±0.6 mg/kg, about 1.67±0.5 mg/kg, about 1.67±0.4 mg/kg, about 1.67±0.3 mg/kg, about 1.67±0.2 mg/kg, or about 1.67±0.1 mg/kg (e.g., about 1.67 mg/kg); or about 1.0±0.5 mg/kg, about 1.0±0.4 mg/kg, about 1.0±0.3 mg/kg, about 1.0±0.2 mg/kg, or about 1.0±0.1 mg/kg (e.g., about 1.0 mg/kg).

In some embodiments, tezampanel, the pharmaceutically acceptable salt thereof, or the prodrug thereof is administered at a dosage of:

- about 0.8±0.5 mg/kg, about 0.8±0.4 mg/kg, about 0.8±0.3 mg/kg, about 0.8±0.2 mg/kg, about 0.8±0.1 mg/kg, about 0.8±0.05 mg/kg, about 0.8±0.04 mg/kg, about 0.8±0.03 mg/kg, about 0.8±0.02 mg/kg, or about 0.8±0.01 mg/kg (e.g., about 0.8 mg/kg);
- about 0.4±0.2 mg/kg, about 0.4±0.1 mg/kg, about 0.4±0.05 mg/kg, about 0.4±0.04 mg/kg, about 0.4±0.03 mg/kg, about 0.4±0.02 mg/kg, or about 0.4±0.01 mg/kg (e.g., about 0.4 mg/kg); or about 0.17±0.05 mg/kg, about 0.17±0.04 mg/kg, about 0.17±0.03 mg/kg, about 0.17±0.02 mg/kg, or about 0.17±0.01 mg/kg (e.g., about 0.17 mg/kg).

In some embodiments, tezampanel, the pharmaceutically acceptable salt thereof, or the prodrug thereof is administered at a dosage of about 10.0±1.0 mg/kg, about 10.0±0.9 mg/kg, about 10.0±0.8 mg/kg, about 10.0±0.7 mg/kg, about 10.0±0.6 mg/kg, about 10.0±0.5 mg/kg, about 10.0±0.4 mg/kg, about 10.0±0.3 mg/kg, about 10.0±0.2 mg/kg, or about 10.0±0.1 mg/kg (e.g., about 10.0 mg/kg).

In some embodiments, tezampanel, the pharmaceutically acceptable salt thereof, or the prodrug thereof is administered at a dosage of about 1.83±1.0 mg/kg, about 1.83±0.9 mg/kg, about 1.83±0.8 mg/kg, about 1.83±0.7 mg/kg, about 1.83±0.6 mg/kg, about 1.83±0.5 mg/kg, about 1.83±0.4 mg/kg, about 1.83±0.3 mg/kg, about 1.83±0.2 mg/kg, or about 1.83=0.1 mg/kg (e.g., about 1.83 mg/kg).

In some embodiments, tezampanel, the pharmaceutically acceptable salt thereof, or the prodrug thereof is administered at a dosage of about 1.67±1.0 mg/kg, about 1.67±0.9 mg/kg, about 1.67±0.8 mg/kg, about 1.67±0.7 mg/kg, about 1.67±0.6 mg/kg, about 1.67±0.5 mg/kg, about 1.67±0.4 mg/kg, about 1.67±0.3 mg/kg, about 1.67±0.2 mg/kg, or about 1.67±0.1 mg/kg (e.g., about 1.67 mg/kg).

In some embodiments, tezampanel, the pharmaceutically acceptable salt thereof, or the prodrug thereof is administered at a dosage of about 0.17±0.05 mg/kg, about 0.17±0.04 mg/kg, about 0.17±0.03 mg/kg, about 0.17±0.02 mg/kg, or about 0.17±0.01 mg/kg (e.g., about 0.17 mg/kg).

Further Administration of Benzodiazepines

In some embodiments, the treatment or prevention further comprises administering to the subject a therapeutically effective amount of a benzodiazepine, a pharmaceutically acceptable salt thereof, or a prodrug thereof.

The term "benzodiazepine", as used here, refers to a compound with a core chemical structure being the fusion of a benzene ring and a diazepine ring.

In some embodiments, the benzodiazepine is clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam.

In some embodiments, the benzodiazepine is clorazepate, diazepam, flurazepam, halazepam, or prazepam.

In some embodiments, the benzodiazepine is lorazepam, lormetazepam, oxazepam, or temazepam.

In some embodiments, the benzodiazepine is clonazepam, flunitrazepam, nimetazepam, or nitrazepam.

In some embodiments, the benzodiazepine is adinazolam, alprazolam, estazolam, or triazolam.

In some embodiments, the benzodiazepine is climazolam, loprazolam, or midazolam.

In some embodiments, the therapeutically effective amount of the benzodiazepine, the pharmaceutically acceptable salt thereof, or the prodrug thereof alleviates an adversing effect of the benzodiazepine.

In some embodiments, the adversing effect is a sedating effect.

In some embodiments, benzodiazepine, the pharmaceutically acceptable salt thereof, or the prodrug thereof is administered in an oral dosage form (e.g., a tablet).

In some embodiments, benzodiazepine, the pharmaceutically acceptable salt thereof, or the prodrug thereof is administered in a parenteral dosage form (e.g., an intravenous dosage form, an intramuscular dosage form, a subcutaneous dosage form, or an intradermal dosage form).

In some embodiments, benzodiazepine, the pharmaceutically acceptable salt thereof, or the prodrug thereof is administered at a dosage of:

about 1.0±0.5 mg/kg, about 1.0±0.4 mg/kg, about 1.0±0.3 mg/kg, about 1.0±0.2 mg/kg, or about 1.0±0.1 mg/kg (e.g., about 1.0 mg/kg); or about 0.1±0.05 mg/kg, about 0.1±0.04 mg/kg, about 0.1±0.03 mg/kg, about 0.1±0.02 mg/kg, or about 0.1±0.01 mg/kg (e.g., about 0.1 mg/kg).

In some embodiments, benzodiazepine, the pharmaceutically acceptable salt thereof, or the prodrug thereof is administered at a dosage of:

about 0.16±0.05 mg/kg, about 0.16±0.04 mg/kg, about 0.16±0.03 mg/kg, about 0.16±0.02 mg/kg, or about 0.16±0.01 mg/kg (e.g., about 0.16 mg/kg); or about 0.016±0.005 mg/kg, about 0.016±0.004 mg/kg, about 0.016±0.003 mg/kg, about 0.016±0.002 mg/kg, or about 0.016±0.001 mg/kg (e.g., about 0.016 mg/kg).

EXEMPLARY EMBODIMENTS

Exemplary Embodiment No. 1. A method of treating or preventing a condition in a subject, comprising administering to the subject a therapeutically effective amount of tezampanel, a pharmaceutically acceptable salt thereof, or a prodrug thereof.

Exemplary Embodiment No. 2. Tezampanel, a pharmaceutically acceptable salt thereof, or a prodrug thereof for use in the treatment or prevention of a condition in a subject.

Exemplary Embodiment No. 3. Use of tezampanel, a pharmaceutically acceptable salt thereof, or a prodrug thereof, in the manufacture of a medicament for the treatment or prevention of a condition in a subject.

Exemplary Embodiment No. 4. The method, tezampanel or the pharmaceutically acceptable salt or prodrug thereof, or use of any one of the preceding Exemplary Embodiments, wherein the subject is an animal.

Exemplary Embodiment No. 5. The method, tezampanel or the pharmaceutically acceptable salt or prodrug thereof, or use of any one of the preceding Exemplary Embodiments, wherein wherein the subject is a human.

Exemplary Embodiment No. 6. The method, tezampanel or the pharmaceutically acceptable salt or prodrug thereof, or use of any one of the preceding Exemplary Embodiments, wherein the subject is an adult.

Exemplary Embodiment No. 7. The method, tezampanel or the pharmaceutically acceptable salt or prodrug thereof, or use of any one of the preceding Exemplary Embodiments, wherein the subject has an age ranging from 18 years to 65 years.

Exemplary Embodiment No. 8. The method, tezampanel or the pharmaceutically acceptable salt or prodrug thereof, or use of any one of the preceding Exemplary Embodiments, wherein the subject has a history of opiate use or abuse.

Exemplary Embodiment No. 9. The method, tezampanel or the pharmaceutically acceptable salt or prodrug thereof, or use of any one of the preceding Exemplary Embodiments, wherein the subject is a child.

Exemplary Embodiment No. 10. The method, tezampanel or the pharmaceutically acceptable salt or prodrug thereof, or use of any one of the preceding Exemplary Embodiments, wherein the subject has an age younger than 18 years.

Exemplary Embodiment No. 11. The method, tezampanel or the pharmaceutically acceptable salt or prodrug thereof, or use of any one of the preceding Exemplary Embodiments, wherein the subject is an infant.

Exemplary Embodiment No. 12. The method, tezampanel or the pharmaceutically acceptable salt or prodrug thereof, or use of any one of the preceding Exemplary Embodiments, wherein the subject has an age of 2 years or younger.

Exemplary Embodiment No. 13. The method, tezampanel or the pharmaceutically acceptable salt or prodrug thereof, or use of any one of the preceding Exemplary Embodiments, wherein the subject has an age of 1 year or younger.

Exemplary Embodiment No. 14. The method, tezampanel or the pharmaceutically acceptable salt or prodrug thereof, or use of any one of the preceding Exemplary Embodiments, wherein the subject has an age of 9 months or younger, 6 months or younger, 5 months or younger, 4 months or younger, 3 months or younger, 2 months or younger, or 1 month or younger.

Exemplary Embodiment No. 15. The method, tezampanel or the pharmaceutically acceptable salt or prodrug thereof, or use of any one of the preceding Exemplary Embodiments, wherein the maternal parent of the subject has a history of opiate use or abuse.

Exemplary Embodiment No. 16. The method, tezampanel or the pharmaceutically acceptable salt or prodrug thereof, or use of any one of the preceding Exemplary Embodiments, wherein the subject has been subjected to in-utero exposure to the opiate.

Exemplary Embodiment No. 17. The method, tezampanel or the pharmaceutically acceptable salt or prodrug thereof, or use of any one of the preceding Exemplary Embodiments, wherein the condition is associated with opiate withdrawal.

Exemplary Embodiment No. 18. The method, tezampanel or the pharmaceutically acceptable salt or prodrug thereof, or use of any one of the preceding Exemplary Embodiments, wherein the condition is a symptom associated with opiate withdrawal.

Exemplary Embodiment No. 19. The method, tezampanel or the pharmaceutically acceptable salt or prodrug thereof, or use of any one of the preceding Exemplary Embodiments, wherein the condition is associated with a disease.

Exemplary Embodiment No. 20. The method, tezampanel or the pharmaceutically acceptable salt or prodrug thereof, or use of any one of the preceding Exemplary Embodiments, wherein the condition is a symptom of a disease.

Exemplary Embodiment No. 21. The method, tezampanel or the pharmaceutically acceptable salt or prodrug thereof, or use of any one of the preceding Exemplary Embodiments, wherein the subject does not intake the opiate within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

Exemplary Embodiment No. 22. The method, tezampanel or the pharmaceutically acceptable salt or prodrug thereof, or use of any one of the preceding Exemplary Embodiments, wherein the subject has a reduced urine concentration for the opiate, as measured by urinalysis, within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

Exemplary Embodiment No. 23. The method, tezampanel or the pharmaceutically acceptable salt or prodrug thereof, or use of any one of the preceding Exemplary Embodiments, wherein the subject is substantially free of the opiate, as measured by urinalysis, within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

Exemplary Embodiment No. 24. The method, tezampanel or the pharmaceutically acceptable salt or prodrug thereof, or use of any one of the preceding Exemplary Embodiments, wherein the subject has a urine concentration for the opiate being lower than about 2000 ng/ml, about 1500 ng/ml, about 1000 ng/ml, about 500 ng/ml, about 400 ng/ml, about 300 ng/ml, about 200 ng/ml, about 100 ng/ml, about 50 ng/ml, about 25 ng/ml, or about 10 ng/ml, as measured by urinalysis within about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

Exemplary Embodiment No. 25. The method, tezampanel or the pharmaceutically acceptable salt or prodrug thereof, or use of any one of the preceding Exemplary Embodiments, wherein the subject has a urine concentration for the opiate being lower than the cutoff levels described in Table 1, as measured by urinalysis about 1 hour, about 2 hours, about 3 hours, about 4 hours, about 5 hours, about 6 hours, about 12 hours, about 18 hours, about 1 day, about 2 days, about 3 days, about 4 days, about 5 days, about 6 days, about 1 week, about 2 weeks, or about 3 weeks, prior to the treatment or prevention.

Exemplary Embodiment No. 26. The method, tezampanel or the pharmaceutically acceptable salt or prodrug thereof, or use of any one of the preceding Exemplary Embodiments, wherein the subject does not intake the opiate during the treatment or prevention.

Exemplary Embodiment No. 27. The method, tezampanel or the pharmaceutically acceptable salt or prodrug thereof, or use of any one of the preceding Exemplary Embodiments, wherein the subject intakes the opiate during the treatment or prevention.

Exemplary Embodiment No. 28. The method, tezampanel or the pharmaceutically acceptable salt or prodrug thereof, or use of any one of the preceding Exemplary Embodiments, wherein the subject has an increased urine concentration for the opiate, as measured by urinalysis, during the treatment or prevention.

Exemplary Embodiment No. 29. The method, tezampanel or the pharmaceutically acceptable salt or prodrug thereof, or use of any one of the preceding Exemplary Embodiments, wherein the subject has a urine concentration for the opiate being lower than about 2000 ng/ml, about 1500 ng/ml, about 1000 ng/ml, about 500 ng/ml, about 400 ng/ml, about 300 ng/ml, about 200 ng/ml, about 100 ng/ml, about 50 ng/ml, about 25 ng/ml, or about 10 ng/ml, as measured by urinalysis during the treatment or prevention.

Exemplary Embodiment No. 30. The method, tezampanel or the pharmaceutically acceptable salt or prodrug thereof, or use of any one of the preceding Exemplary Embodiments, wherein the subject has a urine concentration for the opiate being lower than the cutoff levels described in Table 1, as measured by urinalysis during the treatment or prevention.

Exemplary Embodiment No. 31. The method, tezampanel or the pharmaceutically acceptable salt or prodrug thereof, or use of any one of the preceding Exemplary Embodiments, wherein the urinalysis is point of care (POC) urinalysis.

Exemplary Embodiment No. 32. The method, tezampanel or the pharmaceutically acceptable salt or prodrug thereof, or use of any one of the preceding Exemplary Embodiments, wherein the opiate is codeine, heroin, hydrocodone, hydromorphone, methadone, meperidine, morphine, or oxycodone.

Exemplary Embodiment No. 33. The method, tezampanel or the pharmaceutically acceptable salt or prodrug thereof, or use of any one of the preceding Exemplary Embodiments, wherein the opiate withdrawal is codeine withdrawal, heroin withdrawal, hydrocodone withdrawal, hydromorphone withdrawal, methadone withdrawal, meperidine withdrawal, morphine withdrawal, or oxycodone withdrawal.

Exemplary Embodiment No. 34. The method, tezampanel or the pharmaceutically acceptable salt or prodrug thereof, or use of any one of the preceding Exemplary Embodiments, wherein the hydrocodone withdrawal is Vicodin withdrawal.

Exemplary Embodiment No. 35. The method, tezampanel or the pharmaceutically acceptable salt or prodrug thereof, or use of any one of the preceding Exemplary Embodiments, wherein the hydromorphone withdrawal is Dilaudid withdrawal.

Exemplary Embodiment No. 36. The method, tezampanel or the pharmaceutically acceptable salt or prodrug thereof, or use of any one of the preceding Exemplary Embodiments, wherein the meperidine withdrawal is Demerol withdrawal.

Exemplary Embodiment No. 37. The method, tezampanel or the pharmaceutically acceptable salt or prodrug thereof, or use of any one of the preceding Exemplary Embodiments, wherein the oxycodone withdrawal is Percocet withdrawal.

Exemplary Embodiment No. 38. The method, tezampanel or the pharmaceutically acceptable salt or prodrug thereof, or use of any one of the preceding Exemplary Embodiments, wherein the oxycodone withdrawal is Oxycontin withdrawal.

Exemplary Embodiment No. 39. The method, tezampanel or the pharmaceutically acceptable salt or prodrug thereof, or use of any one of the preceding Exemplary Embodiments, wherein the symptom is drug craving, anxiety, nausea, vomiting, pain, diarrhea, sweating, sneezing, fever, or an increased heart rate.

Exemplary Embodiment No. 40. The method, tezampanel or the pharmaceutically acceptable salt or prodrug thereof, or use of any one of the preceding Exemplary Embodiments, wherein the pain is muscle ache.

Exemplary Embodiment No. 41. The method, tezampanel or the pharmaceutically acceptable salt or prodrug thereof, or use of any one of the preceding Exemplary Embodiments, wherein the administration reduces the frequency, severity, and/or duration of the symptom associated with opiate withdrawal.

Exemplary Embodiment No. 42. The method, tezampanel or the pharmaceutically acceptable salt or prodrug thereof, or use of any one of the preceding Exemplary Embodiments, wherein the frequency, severity, and/or duration of the symptom associated with opiate withdrawal is measured by Clinical Opiate Withdrawal Scale (COWS) score.

Exemplary Embodiment No. 43. The method, tezampanel or the pharmaceutically acceptable salt or prodrug thereof, or use of any one of the preceding Exemplary Embodiments, wherein the COWS score is measured as described in Table 2.

Exemplary Embodiment No. 44. The method, tezampanel or the pharmaceutically acceptable salt or prodrug thereof, or use of any one of the preceding Exemplary Embodiments, wherein prior to administration, the symptom associated with opiate withdrawal has a COWS score of about 5 or greater, about 6 or greater, about 7 or greater, about 8 or greater, about 9 or greater, about 10 or greater, about 11 or greater, or about 12 or greater.

Exemplary Embodiment No. 45. The method, tezampanel or the pharmaceutically acceptable salt or prodrug thereof, or use of any one of the preceding Exemplary Embodiments, wherein prior to administration, the symptom associated with opiate withdrawal has a COWS score of about 13 or greater, about 14 or greater, about 15 or greater, about 16 or greater, about 17 or greater, about 18 or greater, about 19 or greater, about 20 or greater, about 21 or greater, about 22 or greater, about 23 or greater, or about 24 or greater.

Exemplary Embodiment No. 46. The method, tezampanel or the pharmaceutically acceptable salt or prodrug thereof, or use of any one of the preceding Exemplary Embodiments, wherein prior to administration, the symptom associated with opiate withdrawal has a COWS score of about 25 or greater, about 26 or greater, about 27 or greater, about 28 or greater, about 29 or greater, about 30 or greater, about 31 or greater, about 32 or greater, about 33 or greater, about 34 or greater, or about 35 or greater.

Exemplary Embodiment No. 47. The method, tezampanel or the pharmaceutically acceptable salt or prodrug thereof, or use of any one of the preceding Exemplary Embodiments, wherein the administration reduces the frequency, severity, and/or duration of the symptom associated with opiate withdrawal, as measured by a COWS score, by about 1 or greater, about 2 or greater, about 3 or greater, about 4 or greater, about 5 or greater, about 6 or greater, about 7 or greater, about 8 or greater, about 9 or greater, about 10 or greater, about 11 or greater, about 12 or greater, about 13 or greater, about 14 or greater, about 15 or greater, about 16 or greater, about 17 or greater, about 18 or greater, about 19 or greater, about 20 or greater, about 21 or greater, about 22 or greater, about 23 or greater, about 24 or greater, about 25 or greater, about 26 or greater, about 27 or greater, about 28 or greater, about 29 or greater, about 30 or greater, about 31 or greater, about 32 or greater, about 33 or greater, about 34 or greater, or about 35 or greater.

Exemplary Embodiment No. 48. The method, tezampanel or the pharmaceutically acceptable salt or prodrug thereof, or use of any one of the preceding Exemplary Embodiments, wherein the administration reduces the frequency, severity, and/or duration of the symptom associated with opiate withdrawal, as measured by a COWS score, by about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36.

Exemplary Embodiment No. 49. The method, tezampanel or the pharmaceutically acceptable salt or prodrug thereof, or use of any one of the preceding Exemplary Embodiments, wherein the administration results into a reduced symptom associated with opiate withdrawal having a COWS score of about 35 or less, about 34 or less, about 33 or less, about 32 or less, about 31 or less, about 30 or less, about 29 or less, about 28 or less, about 27 or less, about 26 or less, or about 25 or less.

Exemplary Embodiment No. 50. The method, tezampanel or the pharmaceutically acceptable salt or prodrug thereof, or use of any one of the preceding Exemplary Embodiments, wherein the administration results into a reduced symptom associated with opiate withdrawal having a COWS score of about 24 or less, about 23 or less, about 22 or less, about 21 or less, about 20 or less, about 19 or less, about 18 or less, about 17 or less, about 16 or less, about 15 or less, about 14 or less, or about 13 or less.

Exemplary Embodiment No. 51. The method, tezampanel or the pharmaceutically acceptable salt or prodrug thereof, or use of any one of the preceding Exemplary Embodiments, wherein the administration results into a reduced symptom associated with opiate withdrawal having a COWS score of about 12 or less, about 11 or less, about 10 or less, about 9 or less, about 8 or less, about 7 or less, about 6 or less, about 5 or less, about 4 or less, about 3 or less, about 2 or less, or about 1 or less.

Exemplary Embodiment No. 52. The method, tezampanel or the pharmaceutically acceptable salt or prodrug thereof, or use of any one of the preceding Exemplary Embodiments, wherein the therapeutically effective amount of tezampanel, the pharmaceutically acceptable salt thereof, or the prodrug thereof alleviates an adversing drug-drug interation (DDI) between tezampanel and the opiate.

Exemplary Embodiment No. 53. The method, tezampanel or the pharmaceutically acceptable salt or prodrug thereof, or use of any one of the preceding Exemplary Embodiments, wherein the adversing drug-drug interation (DDI) is central nervous system (CNS) depression.

Exemplary Embodiment No. 54. The method, tezampanel or the pharmaceutically acceptable salt or prodrug thereof, or use of any one of the preceding Exemplary Embodiments, wherein the adversing drug-drug interation (DDI) is respiratory depression.

Exemplary Embodiment No. 55. The method, tezampanel or the pharmaceutically acceptable salt or prodrug thereof, or use of any one of the preceding Exemplary Embodiments, wherein the adversing drug-drug interation (DDI) is muscle weakness, lethargy, dizziness, disorientation, slurred speech or stuttering, reduced breathing rate, reduced heart rate, constipation, dry mouth, restlessness, agitation, euphoria, blurred vision, altered vision, double vision, memory loss, nausea, vomiting, or any combination thereof.

Exemplary Embodiment No. 56. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered in an oral dosage form.

Exemplary Embodiment No. 57. The method, tezampanel or the pharmaceutically acceptable salt or prodrug thereof, or use of any one of the preceding Exemplary Embodiments, wherein the prodrug of tezampanel is dasolampanel or a pharmaceutically acceptable salt thereof.

Exemplary Embodiment No. 58. The method, tezampanel or the pharmaceutically acceptable salt or prodrug thereof, or use of any one of the preceding Exemplary Embodiments, wherein a therapeutically effective amount of dasolampanel, or the pharmaceutically acceptable salt thereof, is administered in an oral dosage form.

Exemplary Embodiment No. 59. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered in a parenteral dosage form.

Exemplary Embodiment No. 60. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered in an intravenous (IV) dosage form, an intramuscular (IM) dosage form, a subcutaneous (SC) dosage form, or an intradermal (ID) dosage form.

Exemplary Embodiment No. 61. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered once during the treatment or prevention.

Exemplary Embodiment No. 62. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered two or more times during the treatment of opiate withdrawal or for relapse prevention.

Exemplary Embodiment No. 63. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered every one hour, every two hours, every three hours, every four hours, every five hours, every six hours, every seven hours, every eight hours, every nine hours, every ten hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, or every 24 hours.

Exemplary Embodiment No. 64. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 0.10 mg/kg to about 10.0 mg/kg, about 0.15 mg/kg to about 7.5 mg/kg, about 0.20 mg/kg to about 5.0 mg/kg, about 0.25 mg/kg to about 2.5 mg/kg, about 0.30 mg/kg to about 2.0 mg/kg, about 0.35 mg/kg to about 1.85 mg/kg, about 0.40 mg/kg to about 1.70 mg/kg, about 0.45 mg/kg to about 1.65 mg/kg, about 0.50 mg/kg to about 1.60 mg/kg, about 0.55 mg/kg to about 1.55 mg/kg, about 0.65 mg/kg to about 1.50 mg/kg, about 0.70 mg/kg to about 1.45 mg/kg, about 0.75 mg/kg to about 1.40 mg/kg, about 0.80 mg/kg to about 1.35 mg/kg, about 0.85 mg/kg to about 1.30 mg/kg, about 0.90 mg/kg to about 1.25 mg/kg, about 0.95 mg/kg to about 1.20 mg/kg, about 1.00 mg/kg to about 1.15 mg/kg, or about 1.05 mg/kg to about 1.10 mg/kg.

Exemplary Embodiment No. 65. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 1.50 mg/kg to about 2.00 mg/kg, about 1.60 to about 1.95 mg/kg, about 1.70 mg/kg to about 1.90 mg/kg, or about 1.80 mg/kg to about 1.80 mg/kg.

Exemplary Embodiment No. 66. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 1.00 mg/kg to about 2.00 mg/kg, about 1.25 mg/kg to about 1.90 mg/kg, about 1.50 mg/kg to about 1.80 mg/kg, about 1.60 mg/kg to about 1.75 mg/kg, or about 1.65 mg/kg to about 1.70 mg/kg.

Exemplary Embodiment No. 67. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 0.05 mg/kg to about 0.50 mg/kg, about 0.10 mg/kg to about 0.40 mg/kg, about 0.15 mg/kg to about 0.30 mg/kg, or about 0.15 mg/kg to about 0.20 mg/kg.

Exemplary Embodiment No. 68. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 10.0 mg/kg or less, about 7.5 mg/kg or less, about 5.0 mg/kg or less, about 2.5 mg/kg or less, 2.00 mg/kg or less, about 1.95 mg/kg or less, about 1.90 mg/kg or less, about 1.85 mg/kg or less, about 1.80 mg/kg or less, about 1.75 mg/kg or less, about 1.70 mg/kg or less, about 1.65 mg/kg or less, about 1.60 mg/kg or less, about 1.55 mg/kg or less, about 1.50 mg/kg or less, about 1.45 mg/kg or less, about 1.40 mg/kg or less, about 1.35 mg/kg or less, about 1.30 mg/kg or less, about 1.25 mg/kg or less, about 1.20 mg/kg or less, about 1.15 mg/kg or less, about 1.10 mg/kg or less, about 1.05 mg/kg or less, about 1.00 mg/kg or less, about 0.95 mg/kg or less, about 0.90 mg/kg or less, about 0.85 mg/kg or less, about 0.80 mg/kg or less, about 0.75 mg/kg or less, about 0.70 mg/kg or less, about 0.65 mg/kg or less, about 0.60 mg/kg or less, about 0.55 mg/kg or less, about 0.50 mg/kg or less, about 0.45 mg/kg or less, about 0.40 mg/kg or less, about 0.35 mg/kg or less, about 0.30 mg/kg or less, about 0.25 mg/kg or less, about 0.20 mg/kg or less, about 0.15 mg/kg or less, or about 0.10 mg/kg or less.

Exemplary Embodiment No. 69. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of:

about 10.0±1.0 mg/kg, about 10.0±0.9 mg/kg, about 10.0±0.8 mg/kg, about 10.0±0.7 mg/kg, about 10.0±0.6 mg/kg, about 10.0±0.5 mg/kg, about 10.0±0.4 mg/kg, about 10.0±0.3 mg/kg, about 10.0±0.2 mg/kg, or about 10.0±0.1 mg/kg;

about 7.5±1.0 mg/kg, about 7.5±0.9 mg/kg, about 7.5±0.8 mg/kg, about 7.5±0.7 mg/kg, about 7.5±0.6 mg/kg, about 7.5±0.5 mg/kg, about 7.5±0.4 mg/kg, about 7.5±0.3 mg/kg, about 7.5±0.2 mg/kg, or about 7.5±0.1 mg/kg;

about 5.0±2.0 mg/kg, about 5.0±1.5 mg/kg, about 5.0=1.0 mg/kg, about 5.0±0.9 mg/kg, about 5.0±0.8 mg/kg, about 5.0±0.7 mg/kg, about 5.0±0.6 mg/kg, about 5.0±0.5 mg/kg, about 5.0±0.4 mg/kg, about 5.0±0.3 mg/kg, about 5.0±0.2 mg/kg, or about 5.0±0.1 mg/kg;

about 2.5±1.0 mg/kg, about 2.5±0.9 mg/kg, about 2.5±0.8 mg/kg, about 2.5±0.7 mg/kg, about 2.5±0.6 mg/kg, about 2.5±0.5 mg/kg, about 2.5±0.4 mg/kg, about 2.5±0.3 mg/kg, about 2.5±0.2 mg/kg, or about 2.5=0.1 mg/kg;

about 1.83±1.0 mg/kg, about 1.83±0.9 mg/kg, about 1.83±0.8 mg/kg, about 1.83±0.7 mg/kg, about 1.83±0.6 mg/kg, about 1.83±0.5 mg/kg, about 1.83±0.4 mg/kg, about 1.83±0.3 mg/kg, about 1.83±0.2 mg/kg, or about 1.83±0.1 mg/kg;

about 1.67±1.0 mg/kg, about 1.67±0.9 mg/kg, about 1.67±0.8 mg/kg, about 1.67±0.7 mg/kg, about 1.67±0.6 mg/kg, about 1.67±0.5 mg/kg, about 1.67±0.4 mg/kg, about 1.67±0.3 mg/kg, about 1.67±0.2 mg/kg, or about 1.67±0.1 mg/kg; or about 1.0±0.5 mg/kg, about 1.0±0.4 mg/kg, about 1.0±0.3 mg/kg, about 1.0±0.2 mg/kg, or about 1.0±0.1 mg/kg.

Exemplary Embodiment No. 70. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of:

about 0.8±0.5 mg/kg, about 0.8±0.4 mg/kg, about 0.8±0.3 mg/kg, about 0.8±0.2 mg/kg, about 0.8±0.1 mg/kg, about 0.8±0.05 mg/kg, about 0.8±0.04 mg/kg, about 0.8±0.03 mg/kg, about 0.8±0.02 mg/kg, or about 0.8±0.01 mg/kg;

about 0.4±0.2 mg/kg, about 0.4±0.1 mg/kg, about 0.4±0.05 mg/kg, about 0.4±0.04 mg/kg, about 0.4±0.03 mg/kg, about 0.4±0.02 mg/kg, or about 0.4±0.01 mg/kg; or about 0.17±0.05 mg/kg, about 0.17±0.04 mg/kg, about 0.17±0.03 mg/kg, about 0.17±0.02 mg/kg, or about 0.17±0.01 mg/kg.

Exemplary Embodiment No. 71. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 10.0±1.0 mg/kg, about 10.0±0.9 mg/kg, about 10.0±0.8 mg/kg, about 10.0±0.7 mg/kg, about 10.0±0.6 mg/kg, about 10.0±0.5 mg/kg, about 10.0±0.4 mg/kg, about 10.0±0.3 mg/kg, about 10.0±0.2 mg/kg, or about 10.0±0.1 mg/kg.

Exemplary Embodiment No. 72. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 1.83±1.0 mg/kg, about 1.83±0.9 mg/kg, about 1.83±0.8 mg/kg, about 1.83±0.7 mg/kg, about 1.83±0.6 mg/kg, about 1.83±0.5 mg/kg, about 1.83±0.4 mg/kg, about 1.83±0.3 mg/kg, about 1.83±0.2 mg/kg, or about 1.83±0.1 mg/kg.

Exemplary Embodiment No. 73. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 1.67±1.0 mg/kg, about 1.67±0.9 mg/kg, about 1.67±0.8 mg/kg, about 1.67±0.7 mg/kg, about 1.67±0.6 mg/kg, about 1.67±0.5 mg/kg, about 1.67±0.4 mg/kg, about 1.67±0.3 mg/kg, about 1.67±0.2 mg/kg, or about 1.67±0.1 mg/kg.

Exemplary Embodiment No. 74. The method, tezampanel or the pharmaceutically acceptable salt or prodrug thereof, or use of any one of the preceding Exemplary Embodiments, wherein tezampanel, the pharmaceutically acceptable salt thereof, or the prodrug thereof is administered at a dosage of about 0.17±0.05 mg/kg, about 0.17±0.04 mg/kg, about 0.17±0.03 mg/kg, about 0.17±0.02 mg/kg, or about 0.17±0.01 mg/kg.

Exemplary Embodiment No. 75. The method, tezampanel or the pharmaceutically acceptable salt or prodrug thereof, or use of any one of the preceding Exemplary Embodiments, wherein the treatment or prevention further comprises administering to the subject a therapeutically effective amount of a benzodiazepine, a pharmaceutically acceptable salt thereof, or a prodrug thereof.

Exemplary Embodiment No. 76. The method, tezampanel or the pharmaceutically acceptable salt or prodrug thereof, or use of any one of the preceding Exemplary Embodiments, wherein the benzodiazepine is clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam.

Exemplary Embodiment No. 77. The method, tezampanel or the pharmaceutically acceptable salt or prodrug thereof, or use of any one of the preceding Exemplary Embodiments, wherein the benzodiazepine is clorazepate, diazepam, flurazepam, halazepam, or prazepam.

Exemplary Embodiment No. 78. The method, tezampanel or the pharmaceutically acceptable salt or prodrug thereof, or use of any one of the preceding Exemplary Embodiments, wherein the benzodiazepine is lorazepam, lormetazepam, oxazepam, or temazepam.

Exemplary Embodiment No. 79. The method, tezampanel or the pharmaceutically acceptable salt or prodrug thereof, or use of any one of the preceding Exemplary Embodiments, wherein the benzodiazepine is clonazepam, flunitrazepam, nimetazepam, or nitrazepam.

Exemplary Embodiment No. 80. The method, tezampanel or the pharmaceutically acceptable salt or prodrug thereof, or use of any one of the preceding Exemplary Embodiments, wherein the benzodiazepine is adinazolam, alprazolam, estazolam, or triazolam.

Exemplary Embodiment No. 81. The method, tezampanel or the pharmaceutically acceptable salt or prodrug thereof, or use of any one of the preceding Exemplary Embodiments, wherein the benzodiazepine is climazolam, loprazolam, or midazolam.

Exemplary Embodiment No. 82. The method, tezampanel or the pharmaceutically acceptable salt or prodrug thereof, or use of any one of the preceding Exemplary Embodiments, wherein the therapeutically effective amount of the benzodiazepine, the pharmaceutically acceptable salt thereof, or the prodrug thereof alleviates an adversing effect of the benzodiazepine.

Exemplary Embodiment No. 83. The method, tezampanel or the pharmaceutically acceptable salt or prodrug thereof, or use of any one of the preceding Exemplary Embodiments, wherein the adversing effect is a sedating effect.

Exemplary Embodiment No. 84. The method, tezampanel or the pharmaceutically acceptable salt or prodrug thereof, or use of any one of the preceding Exemplary Embodiments, wherein benzodiazepine, the pharmaceutically acceptable salt thereof, or the prodrug thereof is administered in an oral dosage form.

Exemplary Embodiment No. 85. The method, tezampanel or the pharmaceutically acceptable salt or prodrug thereof, or use of any one of the preceding Exemplary Embodiments, wherein the oral dosage form is a solid tablet or liquid elixer.

Exemplary Embodiment No. 86. The method, tezampanel or the pharmaceutically acceptable salt or prodrug thereof, or use of any one of the preceding Exemplary Embodiments, wherein benzodiazepine, the pharmaceutically acceptable salt thereof, or the prodrug thereof is administered in a parenteral dosage form.

Exemplary Embodiment No. 87. The method, tezampanel or the pharmaceutically acceptable salt or prodrug thereof, or use of any one of the preceding Exemplary Embodiments, wherein the parenteral dosage form is an intravenous dosage form, an intramuscular dosage form, a subcutaneous dosage form, or an intradermal dosage form.

Exemplary Embodiment No. 88. The method, tezampanel or the pharmaceutically acceptable salt or prodrug thereof, or use of any one of the preceding Exemplary Embodiments, wherein benzodiazepine, the pharmaceutically acceptable salt thereof, or the prodrug thereof is administered at a dosage of:

about 1.0±0.5 mg/kg, about 1.0±0.4 mg/kg, about 1.0±0.3 mg/kg, about 1.0±0.2 mg/kg, or about 1.0±0.1 mg/kg; or about 0.1±0.05 mg/kg, about 0.1±0.04 mg/kg, about 0.1±0.03 mg/kg, about 0.1±0.02 mg/kg, or about 0.1±0.01 mg/kg.

Exemplary Embodiment No. 89. The method, tezampanel or the pharmaceutically acceptable salt or prodrug thereof, or use of any one of the preceding Exemplary Embodiments, wherein benzodiazepine, the pharmaceutically acceptable salt thereof, or the prodrug thereof is administered at a dosage of:

about 0.16±0.05 mg/kg, about 0.16±0.04 mg/kg, about 0.16±0.03 mg/kg, about 0.16±0.02 mg/kg, or about 0.16±0.01 mg/kg; or about 0.016±0.005 mg/kg, about 0.016±0.004 mg/kg, about 0.016±0.003 mg/kg, about 0.016±0.002 mg/kg, or about 0.016±0.001 mg/kg.

Definitions

The term "about", as used herein, generally means±10% of the value stated. In some embodiments, "about" or "approximately" generally means±9%, ±8%, ±7%, ±6%, ±5%, ±4%, ±3%, ±2%, or ±1% of the stated value.

The term "opiate" or "opioid", as used herein, refers to a substance that, when reaching opioid receptors, have effects similar to those of morphine. It is understood that the opiate can be a substance extracted or refined from natural plant matter, or it can be synthesized. In some embodiments, the opiate is morphine. In some embodiments, the opiate is oxycodone.

The term "drug-drug interaction" or "DDI", as used herein, refers to a change in the action or side effects of a drug caused by concomitant administration with another drug. The drug-drug interaction may involve one drug which alters the pharmacokinetics of another drug, or may result from competition between the two drugs for a single receptor or signaling pathway.

It is understood that tezampanel may be identified with the IUPAC name of (3S,4aR,6R,8aR)-6-[2-(1H-tetrazol-5-yl)ethyl]decahydroisoquinoline-3-carboxylic acid, the CAS No. 150131-78-5, the CAS No. 154652-83-2, the code name LY-293,558, the code name NGX-424, and/or the following chemical structure:

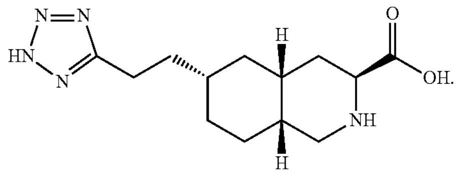 [SMILES: O=C(O)[C@@H]1C[C@H]2C[C@@H](CCc3nn[nH]n3)CC[C@H]2CN1]

In some embodiments, a prodrug of tezampanel may be administered. In some embodiments, the prodrug of tezampanel is dasolampanel. It is understood that dasolampanel may be identified with the IUPAC name of (3S,4aS,6S,8aR)-6-(3-chloro-2-(1H-tetrazol-5-yl)phenoxy) decahydroisoquinoline-3-carboxylic acid, the CAS No. 503294-13-1, and/or the following chemical structure:

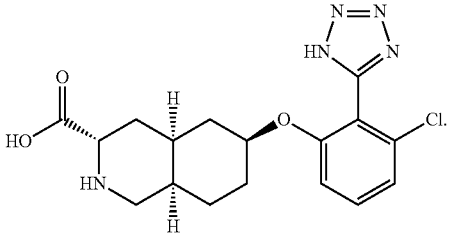 [SMILES: O=C(O)[C@@H]1C[C@H]2C[C@@H](Oc3cccc(Cl)c3-c3nnn[nH]3)CC[C@H]2CN1]

It is understood that morphine may be identified with the IUPAC name of (4R,4aR,7S, 7aR, 12bS)-3-Methyl-2,3,4,4a,7,7a-hexahydro-1H-4,12-methanobenzofuro[3,2-e]isoquinoline-7,9-diol, the CAS No. 52-27-2, and/or the following chemical structure:

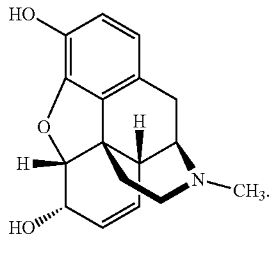

It is understood that lorazepam may be identified with the IUPAC name of 7-Chloro-5-(2-chlorophenyl)-3-hydroxy-1,3-dihydro-1,4-benzodiazepin-2-one, the CAS No. 846-49-1, and/or the following chemical structure:

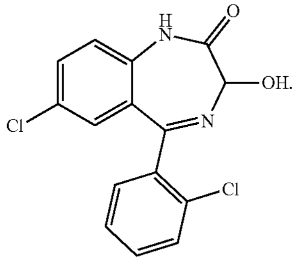 [SMILES: O=C1Nc2ccc(Cl)cc2C(c2ccccc2Cl)=NC1O]

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

It is to be understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure, and are substituted with various groups as described herein.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T. W., Wuts, P. G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a condition or having an increased risk of developing the condition. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "prodrug" refers to any agent which, when administered to a mammal, is converted in whole or in part to a targeted compound. In some embodiments, the prodrug of a compound is also a pharmaceutically acceptable salt of the compound.

It is to be understood that a compound of the present disclosure, or a pharmaceutically acceptable salt, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, 18th edition (1990), Mandell, et al., *Principles and Practice of Infectious Diseases, Saunders Publishing* (8th edition, 2014). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral, inhalational, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Evaluation of Potential Drug-Drug Interation (DDI) Between Tezampanel and Morphine or Lorazepam The purpose of this study is to evaluate the interaction between a test article (tezampanel) and an interaction article (morphine sulphate or lorazepam) and whether such interaction further exacerbates the respiratory depression induced by an opiate or benzodiazepines.

Animals and Instrumentation: Male rats were prepared for surgical implantation of femoral vein catheters and were allowed to recover. Once recovered, animals were placed in whole body plethysmograph chambers and the catheters were passed through ports to the exterior of the chamber which was then sealed. The plethysmograph chambers included transducers that monitored chamber pressure and airflow that change during the respiratory cycles of the indwelling animal.

Treatment Assignments: Animals were placed in chambers for an initial baseline period of 30 minutes where no agents were administered. Following the baseline observation, animals were randomized to receive either a placebo or one of three escalating doses of tezampanel (1.0, 2.5 or 5.0 mg/kg) by intravenous route and respiratory parameters were monitored for an additional 30 minutes. After observing any effects of the placebo or tezampanel doses 30 minutes, animals were then randomized to receive either morphine (10 mg/kg) or lorazepam (1 mg/kg) by the intravenous route and respiratory parameters were monitored for an additional 120 minutes.

Respiratory Monitoring: Pressure and airflow data were continually acquired from the plethysmograph chamber to computer with software than calculated respiratory rate (per minute), the tidal volume (in mL) for each respiratory cycle as well as the minute volume (mL/min) which is the quantity of air respired over 1 minute (FIGS. 1A-1D and 2A-2D).

Example 2. Evaluation of Tezampanel to Attenuate Oxycodone-Precipitated Withdrawal Effects in Mice Male experimentally naive C57BL/6J mice were placed into individual Omnitech photocell activity cages (28×16.5 cm) 30 min after intraperitoneal (i.p.) administration of either vehicle (n=6) or tezampanel at 10 mg/kg (n=7). Interruptions of the photocell beams (two banks of eight cells each) were then recorded for the next 30 min. Data were expressed as number of photocell interruptions.

Statistical analyses. All statistical analyses were performed using Prism 7 (GraphPad Software, La Jolla, CA, USA). Data were analyzed with analysis of variance (ANOVA) followed by the Tukey test for multiple comparisons when appropriate. To determine whether treatment with tezampanel affected oxycodone withdrawal, results with its dosage groups (i.e., chronic oxycodone+tezampanel) were compared to the chronic oxycodone+vehicle treatment group. To determine if tezampanel exerted effects by itself in non-dependent mice, results with the chronic saline+10 mg/kg tezampanel group were compared to the chronic saline+vehicle group. Student's T tests were used for analyzing locomotor activity results. Statistical significance was inferred for all tests when $p<0.05$.

Results and Conclusions

Figure 1A:
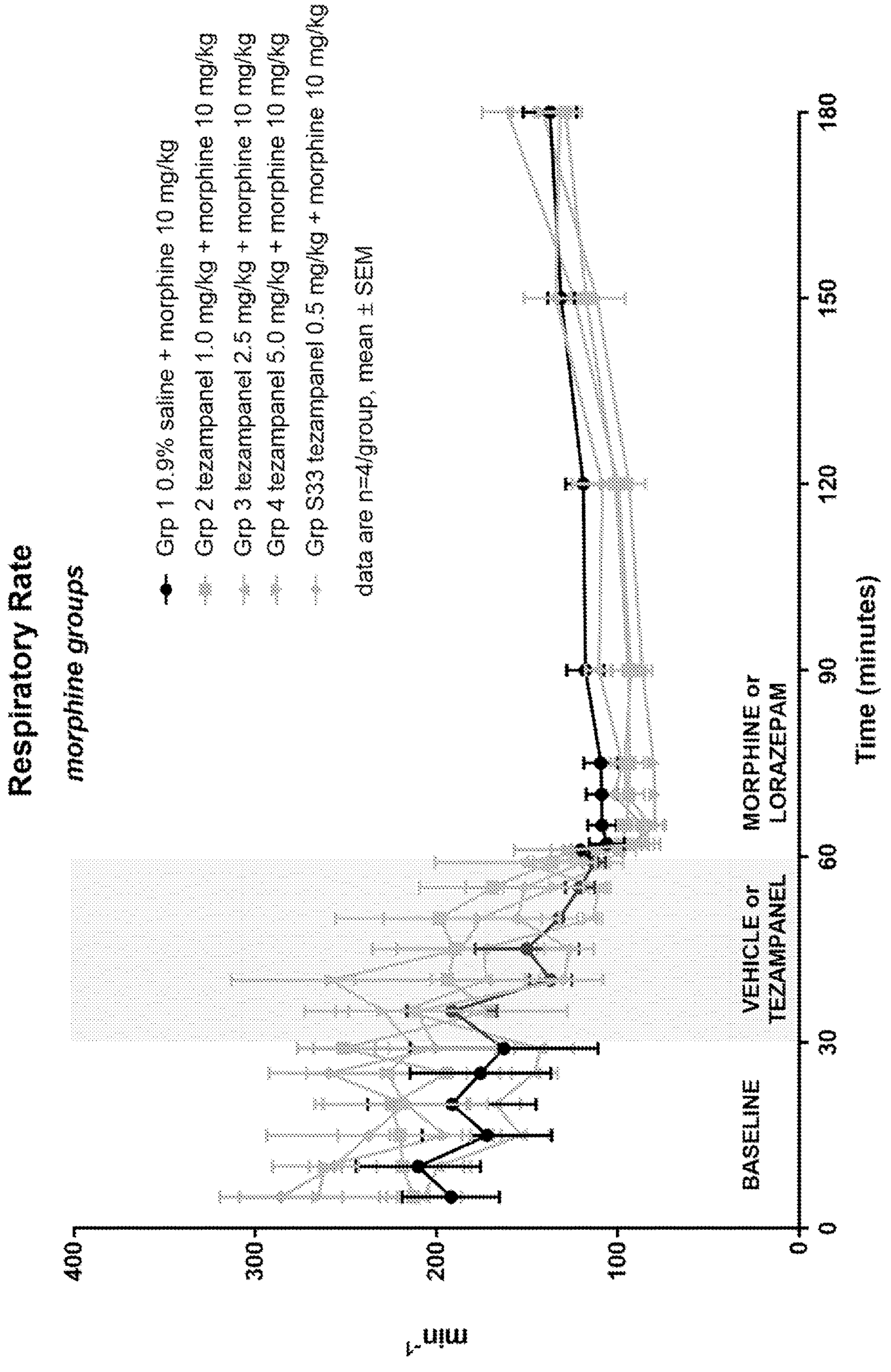
FIGS. 1A-1D are a series of graphs showing the effect of tezampanel and morphine on the respiratory rate, tidal volume, and minute volume of rats.
Figure 1B:
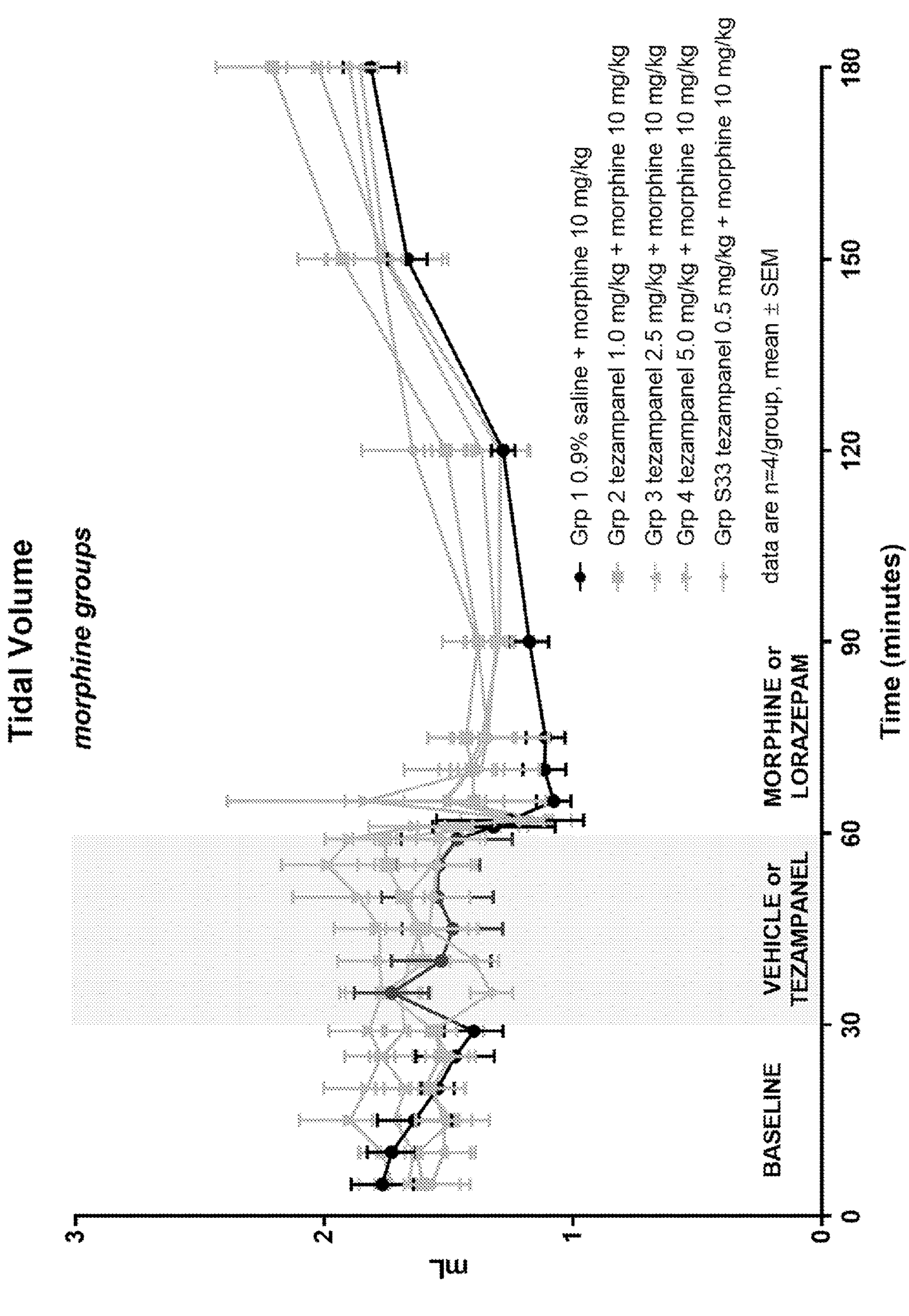
Figure 1C:
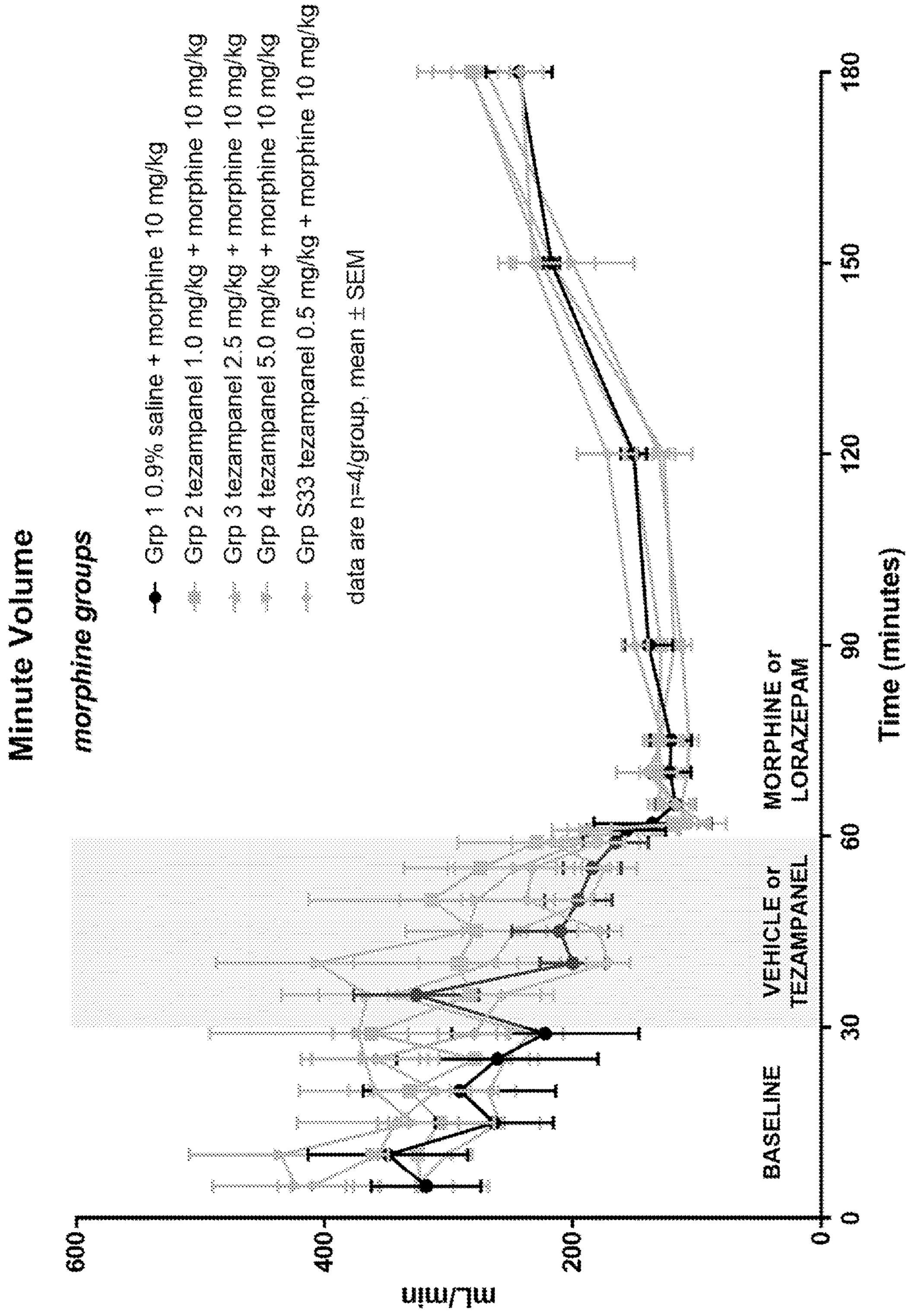
Figure 1D:
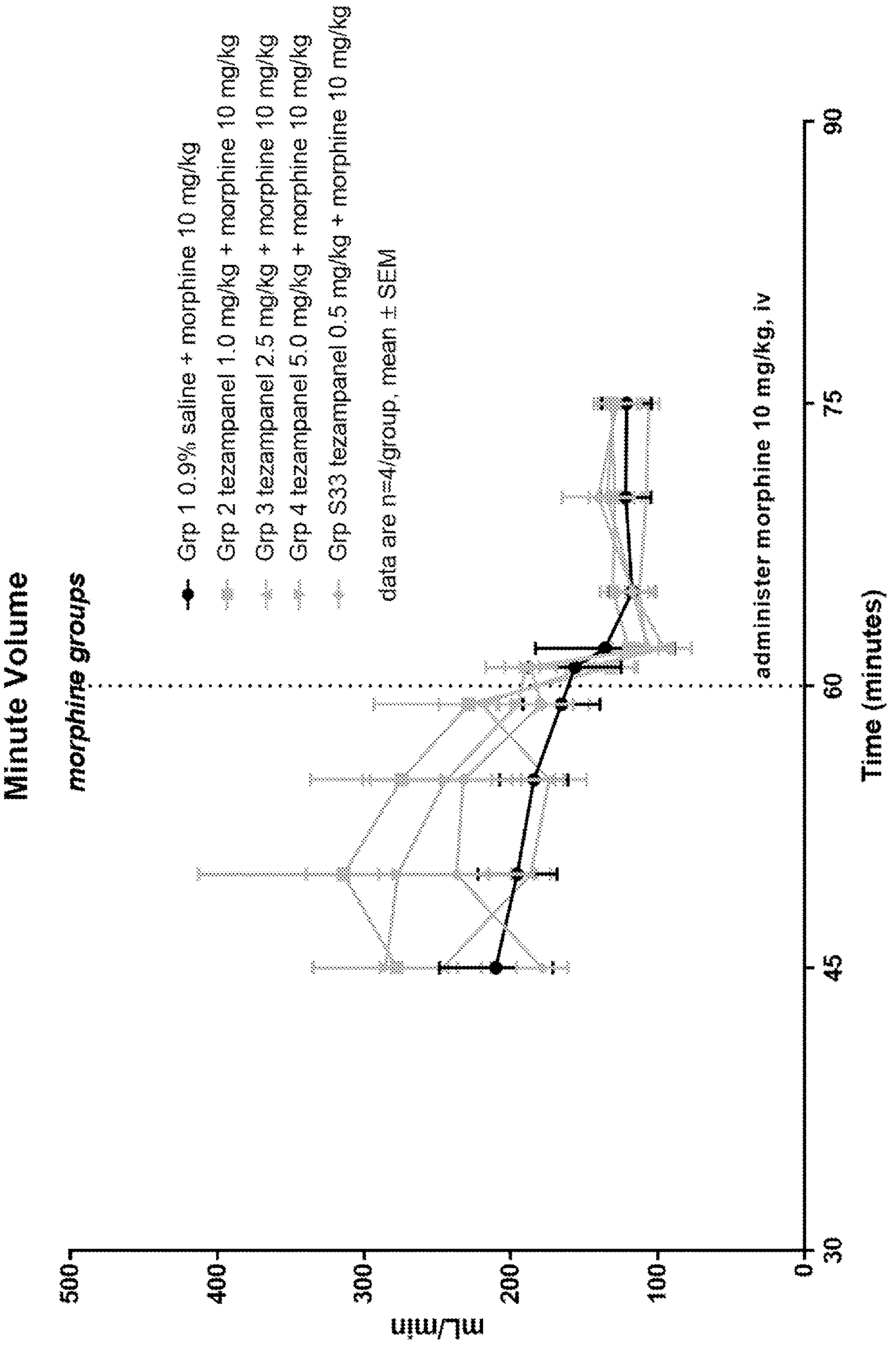
Figure 2A:
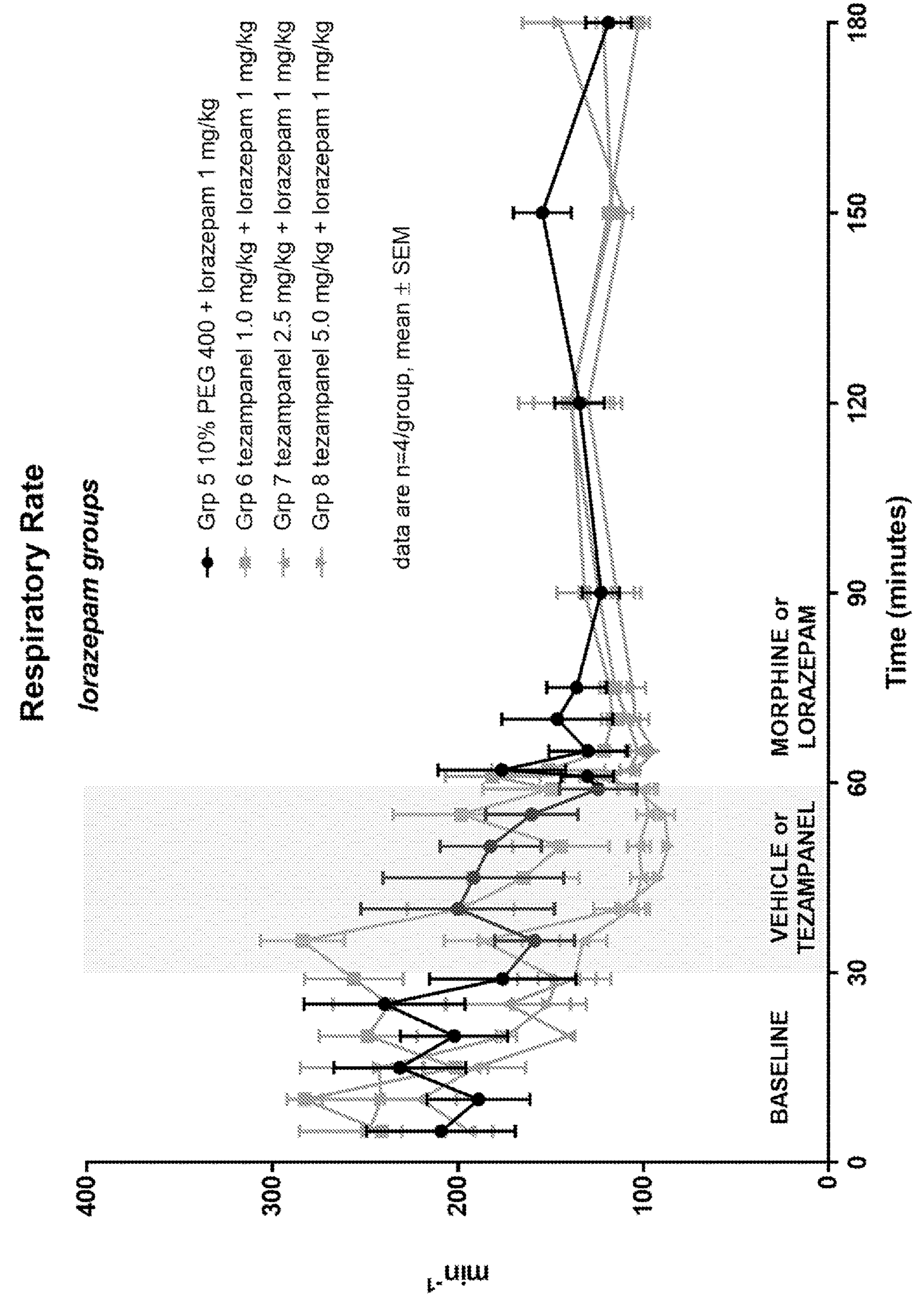
FIGS. 2A-2D are a series of graphs showing the effect of tezampanel and lorazepam on the respiratory rate, tidal volume, and minute volume of rats.
Figure 2B:
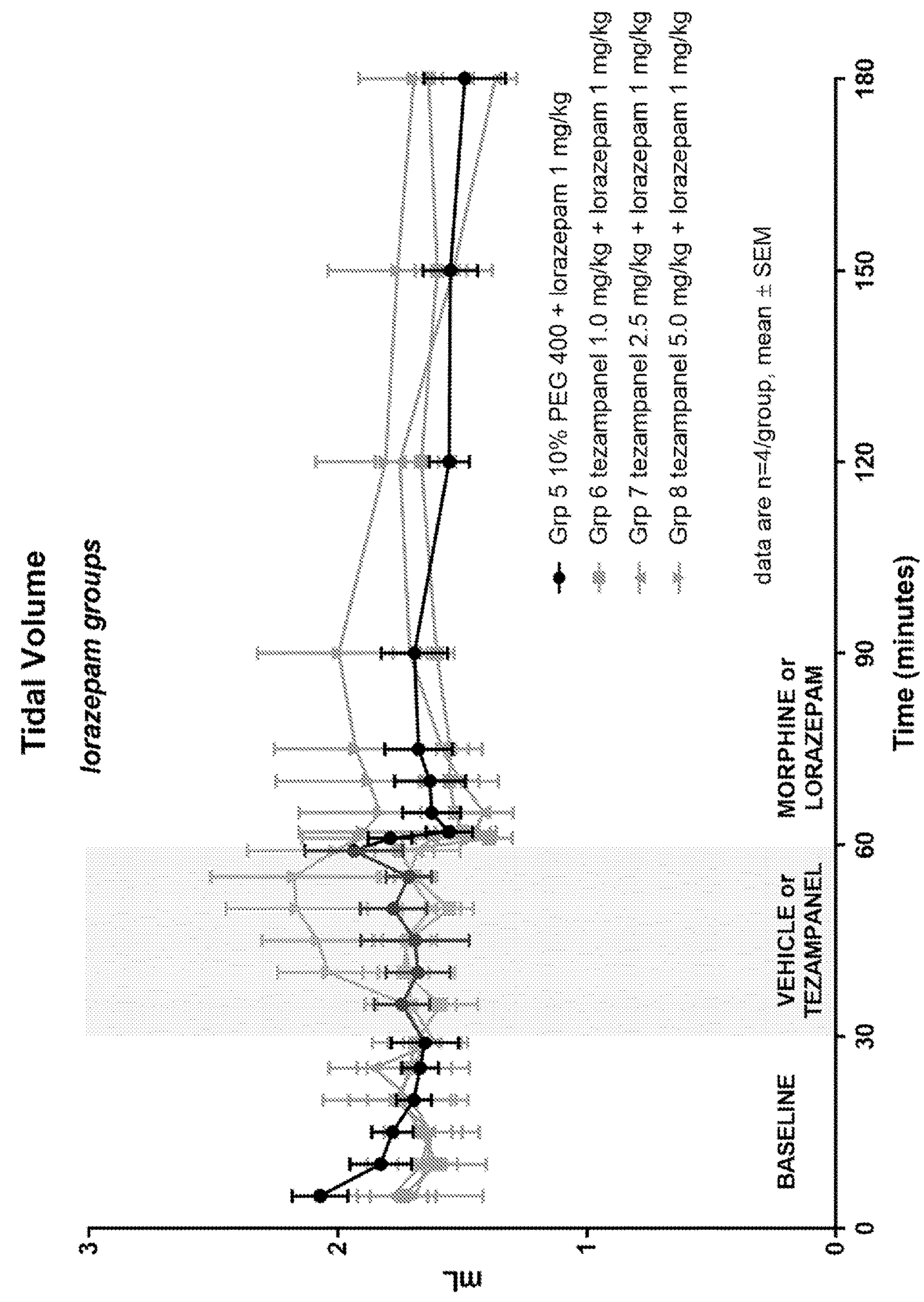
Figure 2C:
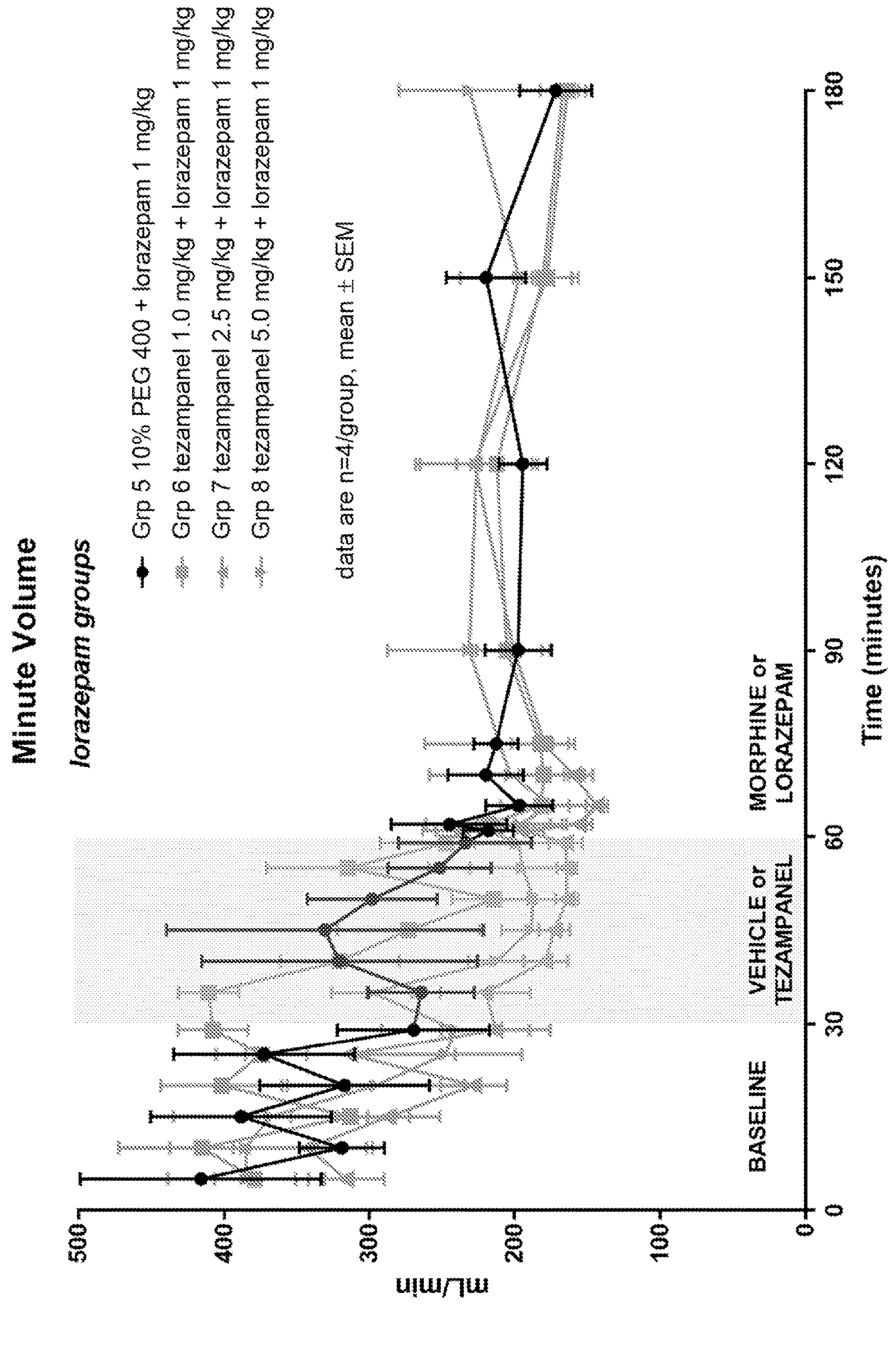
Figure 2D:
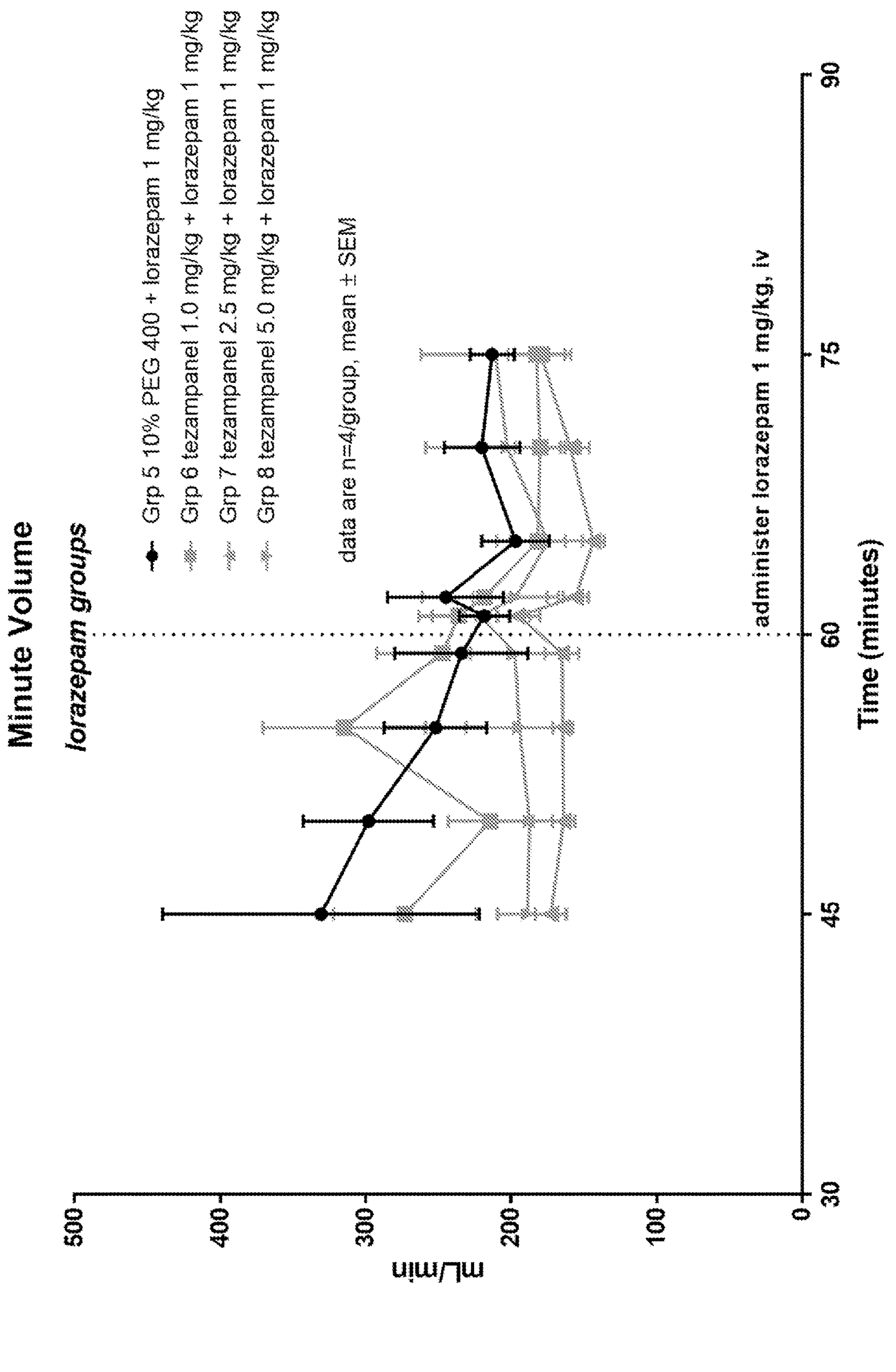
Figure 3A:
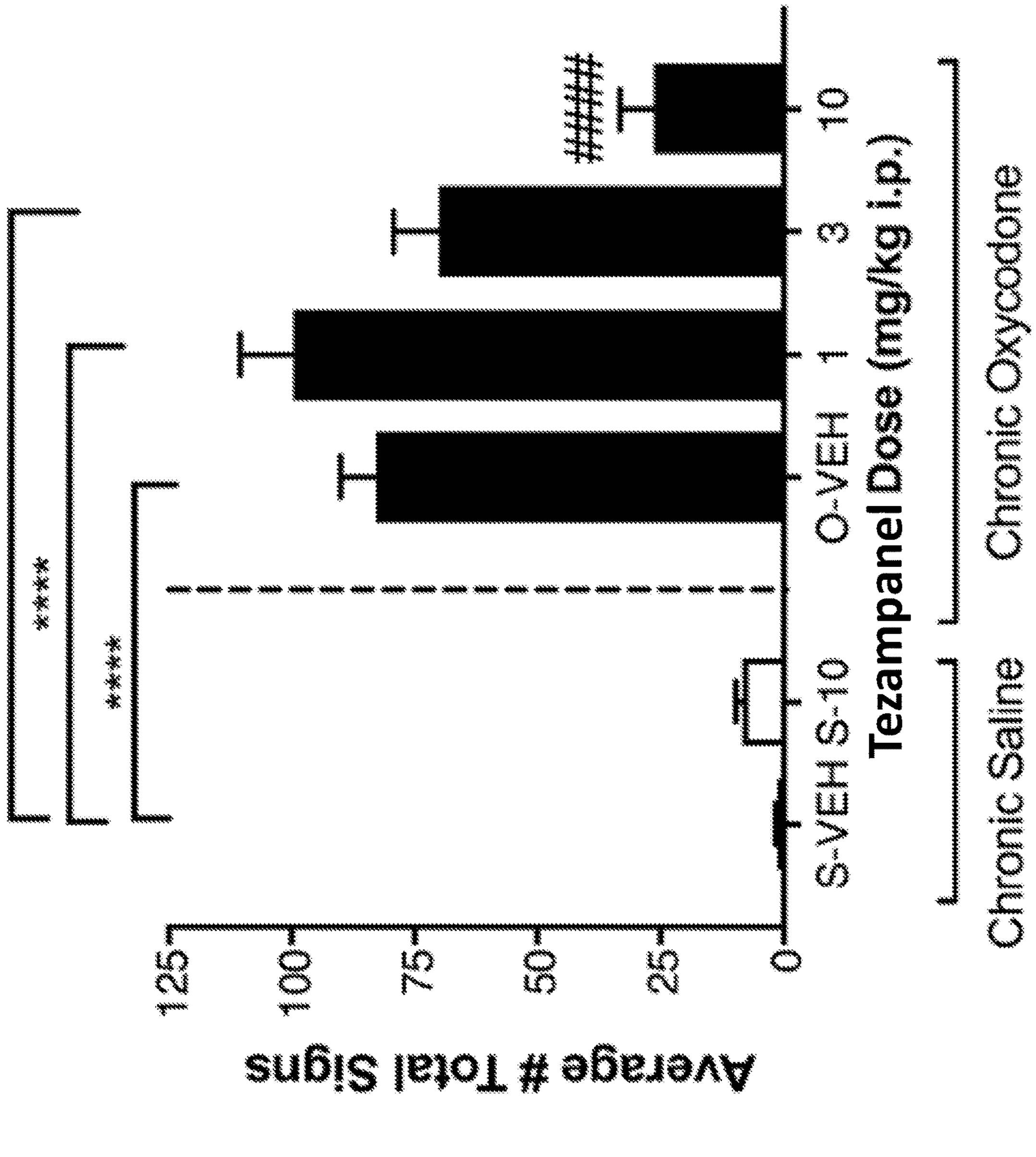
FIG. 3A is a graph showing the effect of tezampanel on oxycodone withdrawal total signs in mice. Each bar represents the mean #S.E.M. of 8 mice per group. ** Denotes significantly different from the group chronically administered saline b.i.d.+vehicle, **=$p \leq 0.0001$. Hash signs denote significantly different from the group chronically administered oxycodone b.i.d.+vehicle: ####=$p \leq 0.0001$. Veh=Vehicle.
Figure 3B:
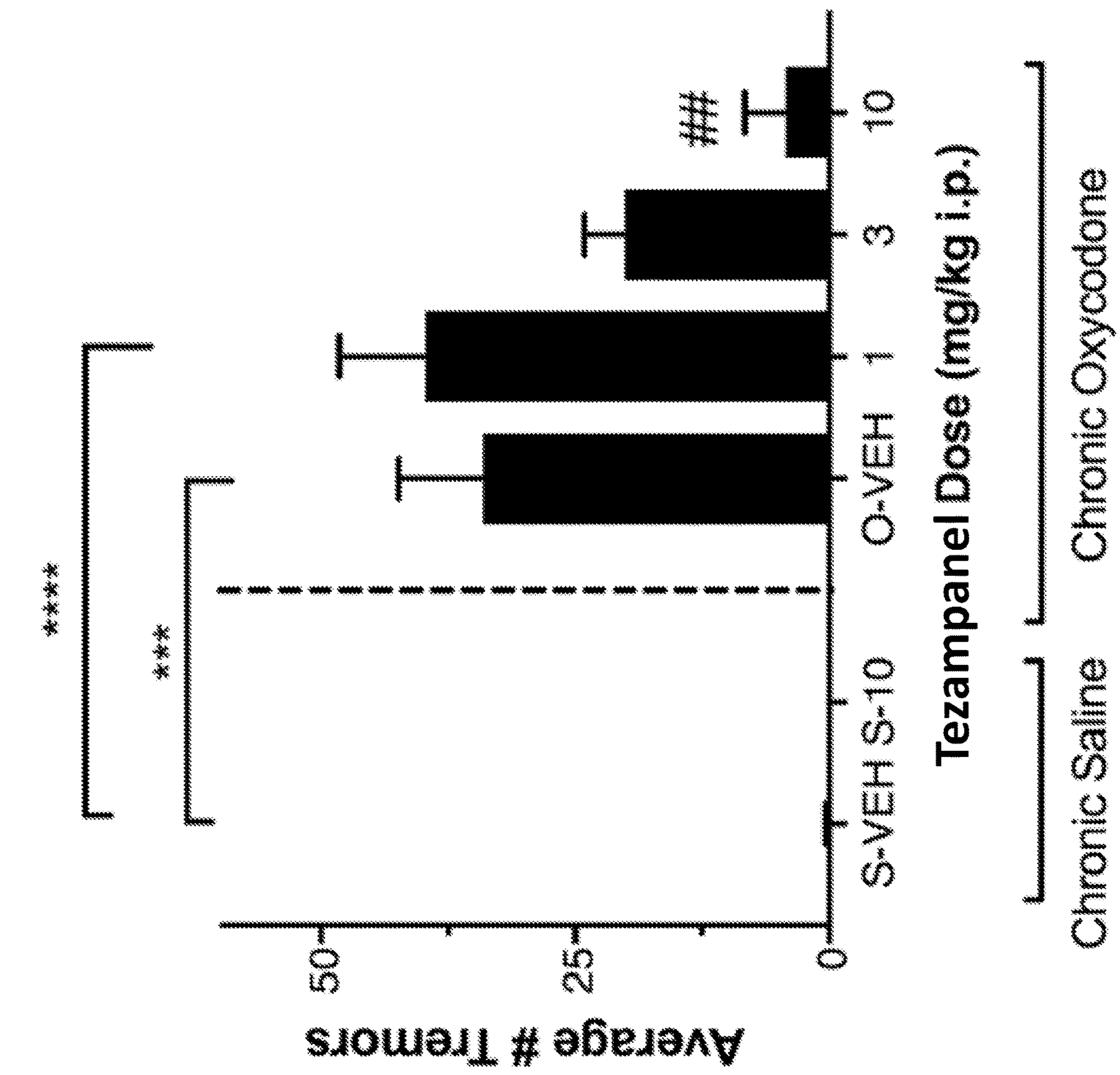
FIG. 3B is a graph showing the effect of tezampanel on oxycodone withdrawal paw tremor signs in mice. Each point represents the mean+S.E.M. of 8 mice per group. * Denotes significantly different from the group chronically administered saline b.i.d.+vehicle, *=$p \leq 0.001$ and ** Denotes significantly different from the group chronically administered saline b.i.d.+vehicle, **=$p<0.0001$. Hash signs denote significantly different from the group chronically administered oxycodone b.i.d.+vehicle: ##=$p<0.01$. Veh=Vehicle.
Figure 3C:
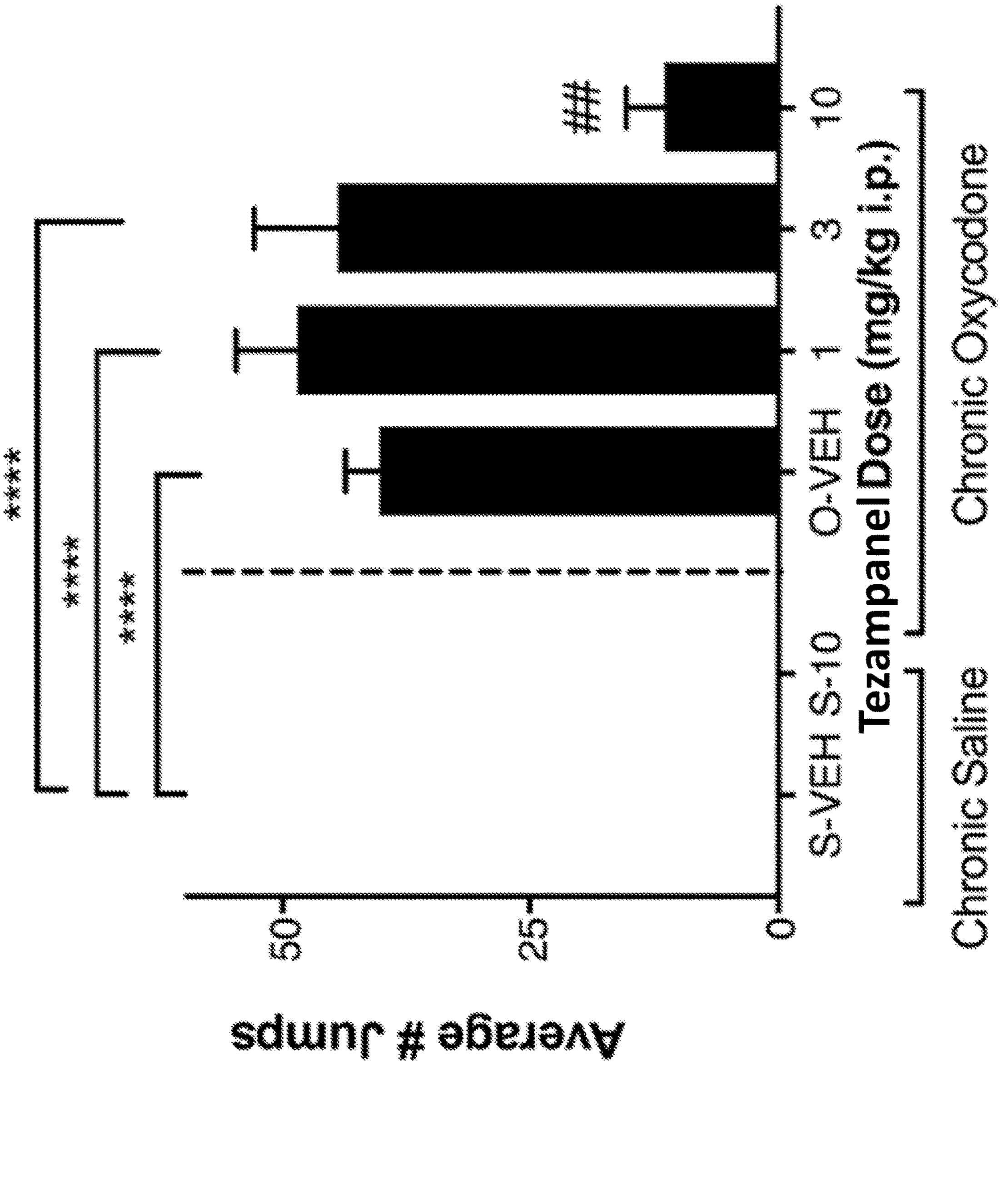
FIG. 3C is a graph showing the effect of tezampanel on oxycodone withdrawal jumping signs in mice. Each point represents the mean #S.E.M. of 8 mice per group. ** Denotes significantly different from the group chronically administered saline b.i.d.+vehicle, **=$p \leq 0.0001$. Hash signs denote significantly different from the group chronically administered oxycodone b.i.d.+vehicle: ##=$p<0.01$. Veh=Vehicle.
Figure 3D:
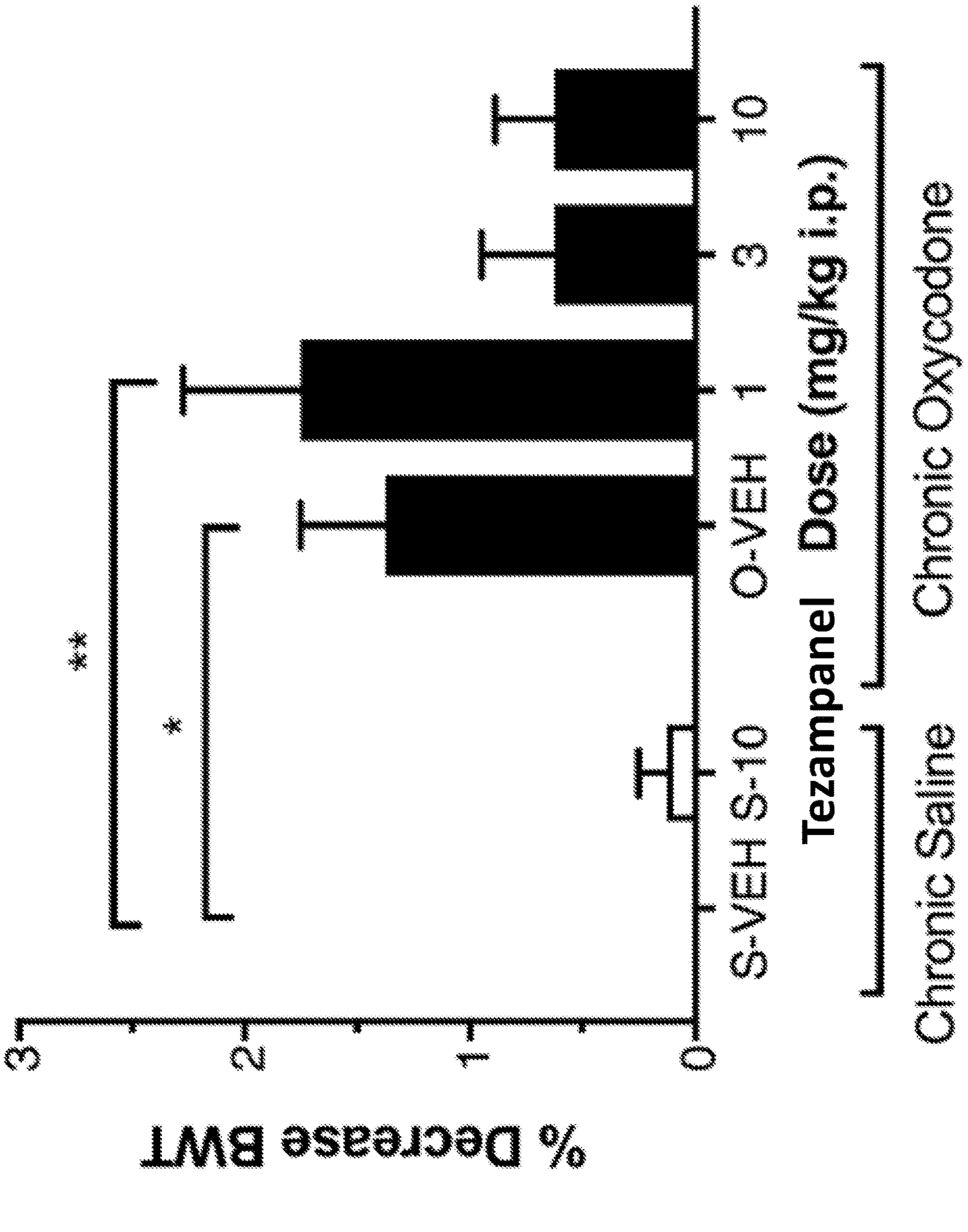
FIG. 3D is a graph showing the effect of tezampanel on oxycodone withdrawal-induced body weight loss in mice. Each point represents the mean #S.E.M. of 8 mice per group.

FIGS. 3A-3D show total withdrawal signs, paw tremors, jumps, and percent body weight loss, respectively. ANOVA results indicated statistically significant total number of signs [$F(5,42)=33.78$; $p<0.0001$] (FIG. 3A), paw tremors [$F(5,42)=10.85$; $p<0.0001$] (FIG. 3B), jumps [$F(5, 42)=22.77$; $p<0.0001$] (FIG. 3C) and loss of body weight [$F(5, 42)=4.694$; $p=0.0017$] (FIG. 3D). Tukey results indicated that mice chronically administered oxycodone and then given vehicle before naloxone on the test day had greater total withdrawal signs ($p<0.0001$), paw tremors ($p=0.0007$), jumps ($p<0.0001$), and loss of body weight ($p=0.0420$) relative to mice similarly treated, but chronically administered saline instead of oxycodone, demonstrating the procedures used were adequate to induce physical dependence upon oxycodone.

Post-hoc analysis revealed that tezampanel attenuated the total number of signs, paw tremors and jumps at the dose of 10 mg/kg, intraperitoneal. However, tezampanel failed to attenuate the decrease in body weight loss at the doses tested. Following chronic treatment with saline, tezampanel (10 mg/kg intraperitoneal) did not have any significant effects on total somatic signs, jumps, paw tremors, or loss of body weight relative to mice similarly treated but administered vehicle on Day 9. In a separate cohort of naive mice, tezampanel at 10 mg/kg intraperitoneal significantly reduced locomotor activity compared to vehicle-treated group ($t=5.999$, $df=11$; $p<0.0001$). Observational comments were made by the technician conducting these studies. Those comments regarded mice that received the 10 mg/kg dose of tezampanel, and the technician noted that the mice showed slowed, unsteady locomotion and low activity rates. Their walking and rearing behaviors appeared to be uncoordinated and off-balance. At times, they would drag their front and hind paws when moving and would have their paws turned completely under while they were sitting. All mice also displayed unprovoked "startled" behaviors once they were asleep or while they were resting (eyes open, but eyelids low). This "startle" response involved jerky movements of their head or entire body. Table 3 denotes the effect of tezampanel on mouse locomotor activity.

TABLE 3

| Treatment | No. of Interruptions (±S.E.M.) |
|---|---|
| Vehicle | 1579.2 ± 119.5 |
| Tezampanel (10 mg/kg, intraperitoneal) | 663.7 ± 87.0**** |

****Denotes significantly different from vehicle, $p < 0.0001$.

Example 3. Evaluation of Effects of Tezampanel on Prime-Induced Reinstatement of Lever Pressing Previously Reinforced by Oxycodone in Rats Tezampanel was tested for its ability to reduce prime-induced reinstatement of extinguished, oxycodone-reinforced lever pressing in rats. Tezampanel doses of 0 (vehicle), 3, and 10 mg/kg were solubilized in a sterile water vehicle and administered i.p. 30 min prior to testing. Levels of responding significantly increased under oxycodone prime conditions relative to extinction levels (i.e., "relapse occurred") in the vehicle but not the Tezampanel treatment groups. Tezampanel significantly decreased reinstated response levels relative to vehicle-control. Overall, these results are consistent with the speculation that Tezampanel would have effectiveness in preventing relapse following an initial lapse in oxycodone use in opioid users as least as determined by these doses and conditions tested.

Subjects

Adult male Long-Evans hooded rats (Envigo, Indianapolis, IN) weighing 275-300 g upon delivery were used. When not in testing, rats were individually housed in standard plastic rodent cages in a temperature-controlled (22° C.), AAALAC-accredited facility in which they had ad libitum access to water. The rats were allowed ad libitum rat chow for at least one week prior to the commencement of training, after which they were maintained at 320 g by controlled feedings. The rats were maintained on a 12-h/12-h reversed light-dark cycle (0600-1800 lights off) for the duration of the experiment, and they were trained and tested during the dark segment of this cycle.

Infusion Assembly System

Catheters were constructed from polyurethane tubing (Access Technologies, Skokie, IL; 0.044" O.D.×0.025" I.D.). The proximal 3.2 cm of the catheter was tapered by stretching following immersion in hot sesame oil. The catheters were prepared with a retaining cuff approximately 3 cm from the proximal end of the catheter. A second retaining cuff was positioned approximately 3.4 cm from the proximal end of the catheter. Magnetic mid-scapula cannula-connectors were obtained from Instech (Plymouth Meeting, PA). These cannula-connectors consisted of magnets embedded in a plastic pedestal containing a port through which passed an “L” shaped section of 22-gauge stainless-steel needle tubing. The lower surface of the pedestal was affixed to a 2.5-cm diameter disc of polyester surgical felt. During sessions, the exposed magnetic portion of the infusion cannula was connected to a magnetic infusion tether consisting of a 35-cm length of 0.40-mm i.d. polypropylene tubing encased within a 30-cm stainless-steel spring to prevent damage. The upper portion of the 0.40 polypropylene tubing was connected to a fluid swivel (Lomir Biomedical, Inc., Quebec, Canada) that was in turn attached via 0.40 polypropylene tubing to the infusion syringe.

Surgical Procedure

Following acclimation to the vivarium, indwelling venous catheters were implanted into the right external jugular vein. Surgical anesthesia was induced with a combination of 50 mg/kg ketamine (KetaVed, Vedco, Inc., St. Joseph, MO) and 8.7 mg/kg xylazine (AnaSed, Lloyd, Inc., Shenandoah, IA). Rats were additionally administered 16 mg/kg oral enrofloxacin (Baytril, Bio-Serv, Frenchtown, NJ) for three days post-surgery, 5 mg/kg carprofen s.c. (Rimadyl, Pfizer Animal Health, New York, NY) before surgery and 6 mg/kg oral carprofen (Rimadyl, Bio-Serv, Frenchtown, NJ) 24 h after surgery. The ventral neck area and back of the rat were shaved and wiped with 7.5% povidone-iodine (BETADINE® Surgical Scrub, Purdue Products L.P., Stamford, CT) and isopropyl alcohol. The rat was placed ventral side down on the surgical table, and a 3-cm incision was made mid-scapula. The rat was then placed dorsal side down on the operating table, and a 2.5-cm incision was made longitudinally through the skin above the jugular area. The underlying fascia was bluntly dissected, and the right external jugular vein isolated and ligated. A small cut was made into the vein using iris or artery scissors, and the catheter was introduced into the vein and inserted up to the level of the second retaining cuff.

The vein encircling the catheter between the two cuffs was then tied with silk suture. A second suture was then used to anchor the catheter to the surrounding fascia. The distal end of the catheter was passed subcutaneously and attached to the cannula-connector that was then inserted subcutaneously through the dorsal incision. The upper post portion of the cannula-connector exited through the mid-scapular incision. Both incisions were then sprayed with a gentamicin sulfate/betamethasone valerate topical antibiotic (Betagen, Med-Pharmex, Inc., Pomona, CA), and the incisions were closed with Michel wound clips or Reflex 9 wound clips.

Rats were allowed to recover from surgery for at least 5 days before self-administration training began. Periodically throughout training, 5 mg/kg ketamine (KetaVed, Vedco, Inc., St. Joseph, MO) or 5 mg/kg methohexital (Brevital, JHP Pharmaceuticals, Rochester, MI) was infused through the catheters to determine patency as inferred when immediate anesthesia was induced. Between sessions, the catheters were flushed and filled with 0.1 ml of a 25% glycerol (Acros, New Jersey)/75% sterile saline locking solution containing: 250 units/ml heparin (Abraxis Pharmaceutical Products, Schaumburg, IL) and 200 mg/ml ampicillin/100 mg/ml sulbactam (Auromedics Pharma, LLC, Dayton, NJ). If, during the experiment, a catheter was determined to be in-patent, the left external jugular was then catheterized, and the rat was returned to testing. During extinction and reinstatement testing, infusions through catheters did not occur, and these catheter maintenance procedures were not employed.

Apparatus

Commercially obtained test chambers equipped with two retractable levers, a 5-w house light, and a Sonalert® tone generator (MED Associates, Inc., St. Albans, VT) were used.

Positioned above each lever was a white cue light. During each session, infusion tubing protected by a stainless-steel spring tether connected the back-mounted pedestal implanted in the mid-scapular area to a counter-balanced liquid swivel suspended above each chamber.

Infusion tubing subsequently connected the other end of the swivel to an infusion pump (Model PHS-100; MED Associates, Inc., St. Albans, VT) that, when activated, delivered a 6-s, 0.07-ml infusion. Recording of lever presses and activation of lights, pumps, and Sonalerts® were accomplished by a microcomputer, interface, and associated software (MED-PCR IV, MED Associates, Inc., St. Albans, VT).

Self-Administration and Extinction Procedures

Oxycodone self-administration training sessions were conducted five days per week (M-F) for 3 h daily. Each response (fixed ratio 1 reinforcement schedule, i.e., “FR1”) on the right-side lever resulted in the delivery of a 0.01 mg/kg oxycodone infusion (0.07 ml/6 s). For the duration of the infusion, the tone sounded, and the stimulus lights above both levers flashed at 3 Hz.

Active (right-side) lever presses during the infusions as well as all inactive (left-side) lever presses were recorded but were without scheduled consequences.

Self-administration training continued until these criteria had been met: 1) at least 12 self-administration sessions had occurred; 2) at least 15 oxycodone infusions had occurred during each of the last four sessions; 3) at least 125 lifetime oxycodone infusions had been obtained; 4) at least 50 active lever responses on the last three days of self-administration had been emitted; and 5) there were no increasing or decreasing trends in active lever responses during the last three sessions of self-administration, after which extinction training began. Subsequently, twelve 3-h daily (Mon-Sun) extinction sessions were conducted. During extinction sessions, the house light was illuminated, and the levers were extended, but infusions were not administered nor did any other scheduled stimulus change occur (i.e., neither Sonalert® activations nor stimulus light illuminations occurred).

Rats were considered eligible for reinstatement testing provided that the mean number of active-lever presses during the last 3 sessions of extinction was lower than the mean number of active-lever presses during the first 3 sessions of extinction. Rats that did not meet this extinction criterion were excluded from subsequent testing.

Testing the Effectiveness of Tezampanel in Preventing Prime-Induced Reinstatement A six-day incubation period during which rats remained in their home cages followed extinction training. Oxycodone prime reinstatement testing immediately followed this incubation period (i.e., on the seventh day following the 12th day of extinction training). Conditions during prime reinstatement testing were identical to those during extinction except that either 3 or 10 mg/kg Tezampanel or its vehicle was administered 30 min prior to the reinstatement test session. Additionally, 0.1 mg/kg s.c. oxycodone was administered 10 min prior to the reinstatement test session (i.e., oxycodone prime). Doses of 0 (vehicle), 3 and 10 mg/kg i.p. of Tezampanel were tested using separate groups of N=12 rats. The rats were assigned to the vehicle group first to confirm the effectiveness of the reinstatement procedure before proceeding with tests with Tezampanel.

Drugs

Oxycodone hydrochloride was obtained commercially (Mallinckrodt, Hazelwood, MO) and was prepared in sterile 0.9% saline. Oxycodone stock solutions were sterilized by filtration through 0.2-μm filtration disks. Oxycodone infusions were delivered in a 6-s, 0.07-ml volume. Heparin, 5 units/ml (Abraxis Pharmaceutical Products, Schaumburg, IL), was additionally added to oxycodone and saline infusates. Tezampanel was supplied by NIDA and was solubilized in a sterile water vehicle. Tezampanel was administered i.p. 30 min prior to testing in a volume equivalent to 1 ml/kg body weight.

Data Analysis

Initially, numbers of active lever presses (i.e., the right-side lever, the presses of which were previously reinforced with oxycodone) during the reinstatement test session were analyzed using the Grubbs test for outliers (Extreme Studentized Deviate), and a rat's data were excluded from its group throughout all subsequent analyses if $p \leq 0.05$.

To determine whether the groups had been trained to self-administer oxycodone and to extinguish responding to comparable levels before reinstatement testing, active lever presses that occurred during the last session of self-administration and the last session of extinction were separately analyzed using individual ANOVAs. If results with an ANOVA were found significant ($p<0.05$), comparisons between each group were conducted using Tukey's Multiple Comparison Tests Numbers of active lever presses during the reinstatement test session for each Tezampanel group were compared to the vehicle group's lever presses using unpaired, two-tailed t-tests. A significant reduction in test-day active lever presses by a test drug group relative to those of the vehicle group would indicate a reduction in relapse levels had occurred. Obtaining a reduction in vehicle reinstatement levels by Tezampanel-treated rats would be considered a primary outcome measure and consistent with a prediction of an ability to attenuate clinical relapse. Numbers of active lever presses during the reinstatement test session for each group were additionally compared to the group's lever presses that occurred during the last session of extinction using paired, one-tailed t-tests. Nonsignificantly greater test-day active lever presses than those occurring during extinction would indicate that relapse had failed to occur. Obtaining a failure to reinstate (relapse) would be considered a secondary outcome measure.

Numbers of inactive lever presses (i.e., presses of the left-side lever) occurring during the test session between groups were compared using an ANOVA. If results with an ANOVA were found significant ($p<0.05$), comparisons between each group were conducted using Tukey's Multiple Comparison Tests. All statistical tests were conducted using microcomputer software (Prism 9 for Macintosh, GraphPad Software, Inc., San Diego, CA), and all types of comparisons were considered statistically significant if $p \leq 0.05$.

Results

FIG. 4A shows the mean numbers of active lever presses emitted during the reinstatement test session for each of the test groups. The mean (+S.E.M.) level of reinstated responses under vehicle-test conditions was 35.42 (+7.112). The mean levels of reinstated responding were 15.55 (+3.022) and 13.00 (+2.537) for the 3 and 10 mg/kg dose groups, respectively. Relative to the vehicle-treated group, Tezampanel reduced responding below vehicle control levels ($t=2.489$, $df=21$, $p=0.0106$ and $t=2.864$, $df=21$, $p=0.0046$ for the 3 and 10 mg/kg Tezampanel groups, respectively).

Mean (+S.E.M.) number of active lever presses during the last session of extinction emitted by the vehicle treatment group was 20.67 (+5.098) and increased to 35.42 (+7.112) during the reinstatement test session which was a statistically significant increase ($t=1.912$, $df=11$, $p=0.0412$), indicating that the conditions used effectively resulted in reinstatement in the vehicle-treated group. Levels of active lever presses during extinction did not significantly increase during the reinstatement test session for Tezampanel dose groups. Individual group extinction means responses (±SEM)/reinstatement test mean responses (±SEM) were: 3 mg/kg: [11.55 (±2.402)/15.55 (±3.022), ($t=1.020$, $df=10$, $p=0.16.59$)] and 10 mg/kg: [14.73 (±2.416)/13.00 (±2.537), ($t=0.6650$, $df=10$, $p=0.2606$)]. These results indicated that treatment with 3 and 10 mg/kg Tezampanel prevented oxycodone prime injections from eliciting effective reinstatement.

Certain rat data were excluded for failing to meet the Grubbs Test evaluation on test-day results. The ANOVA indicated that numbers of active lever presses during the last day of self-administration were significantly different [$F(2, 31)=3.537$; $p=0.0413$] across rats among groups, however, pair-wise Tukey multiple comparisons indicated that there were no significant differences between group pairs (data not shown) indicating that the rats had been trained to self-administer oxycodone to similar levels prior to extinction training. Numbers of active lever presses during the last day of extinction were non-significantly different [$F(2,31)=1.633$; $p=0.2117$] across rats from all groups, indicating that the rats had been extinguished to similar levels prior to reinstatement testing (data not shown). Mean numbers of inactive lever presses (FIG. 4B) were generally low in number during the reinstatement test, although the ANOVA indicated that mean inactive lever presses were significantly different among the groups [$F(2,31)-3.299$; $p=0.0502$]. Tukey multiple comparisons tests indicated that the number of inactive lever presses emitted by the 3 mg/kg Tezampanel group were significantly lower ($P=0.0439$) than those of the vehicle group.

Without wishing to be bound by theory, the vehicle and Tezampanel groups had been trained and extinguished to similar levels. The vehicle but not the Tezampanel groups had their levels of extinguished responding significantly increased and reinstated, or in other words, only the vehicle group relapsed under these experimental conditions. Tezampanel reduced reinstatement test levels of responding below those occurring under vehicle conditions at both the 3 and 10 mg/kg doses. Overall, these results are consistent with the speculation that Tezampanel would have effectiveness in blunting relapse to oxycodone usage resulting from lapses to oxycodone contact, at least as suggested by the dose range tested and the statistical analyses used.

EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating a condition associated with opiate withdrawal or opiate relapse in a subject, comprising administering to the subject a therapeutically effective amount of tezampanel, a pharmaceutically acceptable salt thereof, or a prodrug thereof, wherein the tezampanel, pharmaceutically acceptable salt thereof, or prodrug thereof is administered intravenously, intramuscularly, or subcutaneously at a dose of about 0.5 mg/kg to about 1.5 mg/kg.

2. The method of claim 1, wherein the subject is a human.

3. The method of claim 1, wherein the condition is associated with opiate withdrawal.

4. The method of claim 3, wherein the opiate withdrawal is codeine withdrawal, heroin withdrawal, hydrocodone withdrawal, hydromorphone withdrawal, methadone withdrawal, meperidine withdrawal, morphine withdrawal, or oxycodone withdrawal.

5. The method of claim 1, wherein the subject has a history of opiate use or abuse.

6. The method of claim 1, wherein the maternal parent of the subject has a history of opiate use or abuse.

7. The method of claim 1, wherein the subject has been subjected to in-utero exposure to the opiate.

8. The method of claim 3, wherein the administration reduces the frequency, severity, and/or duration of the symptom associated with opiate withdrawal.

9. The method of claim 3, wherein the frequency, severity, and/or duration of the symptom associated with opiate withdrawal is measured by Clinical Opiate Withdrawal Scale (COWS) score.

10. The method of claim 1, wherein the condition is associated with opiate relapse.

11. The method of claim 10, wherein the opiate relapse is codeine relapse, heroin relapse, hydrocodone relapse, hydromorphone relapse, methadone relapse, meperidine relapse, morphine relapse, or oxycodone relapse.

12. The method of claim 10, wherein the administration reduces the frequency, severity, and/or duration of the symptom associated with opiate relapse.

13. The method of claim 1, wherein the therapeutically effective amount of tezampanel, the pharmaceutically acceptable salt thereof, or the prodrug thereof avoids an adverse drug-drug interaction (DDI) between tezampanel and the opiate.

14. The method of claim 1, wherein the treatment further comprises administering to the subject a therapeutically effective amount of a benzodiazepine, a pharmaceutically acceptable salt thereof, or a prodrug thereof.

15. The method of claim 14, wherein the benzodiazepine is clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam.

16. The method of claim 1, wherein the tezampanel or a pharmaceutically acceptable salt thereof is administered at a dose of about 0.5 mg/kg.

17. The method of claim 1, wherein the tezampanel or a pharmaceutically acceptable salt thereof is administered at a dose of about 1.0 mg/kg.

18. The method of claim 1, wherein the tezampanel or a pharmaceutically acceptable salt thereof is administered at a dose of about 1.5 mg/kg.

19. The method of claim 1, wherein the tezampanel or a pharmaceutically acceptable salt thereof is administered once a day.

20. The method of claim 1, wherein the tezampanel or a pharmaceutically acceptable salt thereof is administered twice a day.

21. The method of claim 20, wherein the first dose is administered in the morning and the second dose is administered approximately 10 hours after the first dose.

22. The method of claim 1, wherein the tezampanel is administered to a subject having a COWS score of about 5 or greater prior to administration.

23. The method of claim 1, wherein tezampanel or a pharmaceutically acceptable salt thereof is administered intravenously or intramuscularly.

24. The method of claim 1, wherein tezampanel or a pharmaceutically acceptable salt thereof is administered intravenously.

25. The method of claim 16, wherein tezampanel or a pharmaceutically acceptable salt thereof is administered intravenously.

26. The method of claim 17, wherein tezampanel or a pharmaceutically acceptable salt thereof is administered intravenously.

27. The method of claim 18, wherein tezampanel or a pharmaceutically acceptable salt thereof is administered intravenously.

* * * * *